(12) United States Patent
Müller et al.

(10) Patent No.: US 12,161,708 B2
(45) Date of Patent: Dec. 10, 2024

(54) COMBINED PROPHYLACTIC AND THERAPEUTIC VACCINES

(71) Applicant: Deutsches Krebsforschungszentrum, Heidelberg (DE)

(72) Inventors: Martin Müller, Neckargemünd (DE); Simone Ottonello, Heidelberg (DE); Xueer Zhao, Dossenheim (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 598 days.

(21) Appl. No.: 15/733,861

(22) PCT Filed: May 29, 2019

(86) PCT No.: PCT/EP2019/064001
§ 371 (c)(1),
(2) Date: Nov. 30, 2020

(87) PCT Pub. No.: WO2019/229142
PCT Pub. Date: Dec. 5, 2019

(65) Prior Publication Data
US 2021/0228702 A1     Jul. 29, 2021

(30) Foreign Application Priority Data

May 30, 2018  (EP) .................................. 18175218

(51) Int. Cl.
*A61K 39/12* (2006.01)
*C07K 16/28* (2006.01)
*A61K 39/00* (2006.01)

(52) U.S. Cl.
CPC .......... *A61K 39/12* (2013.01); *C07K 16/2896* (2013.01); *A61K 2039/55566* (2013.01); *A61K 2039/585* (2013.01); *A61K 2039/6031* (2013.01); *A61K 2039/645* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 7,202,034 | B2 | 4/2007 | Van Der Burg et al. |
| 7,384,636 | B2 | 6/2008 | Nishizawa |
| 7,399,467 | B2 | 7/2008 | Lu et al. |
| 7,829,667 | B2 | 11/2010 | Kim |
| 8,637,039 | B2 * | 1/2014 | Preville ................ A61K 39/385 435/5 |

FOREIGN PATENT DOCUMENTS

| | | | |
|---|---|---|---|
| JP | 2004525115 A | 8/2004 | |
| JP | 2007522108 A | 8/2007 | |
| JP | 2008500813 A | 1/2008 | |
| WO | 2004087767 A1 | 10/2004 | |
| WO | 2007062819 A2 | 6/2007 | |
| WO | 2010070052 A2 | 6/2010 | |
| WO | WO 2017/0754420 * | 5/2017 | ............... C05K 5/18 |
| WO | 2017211886 A1 | 12/2017 | |

OTHER PUBLICATIONS

Canoli et al. (Scientific Reports, 2014, p. 1-11).*
Rubio et al. (Vaccine, 2009, p. 1949-1956).*
K. Bernardeau et al.; A Simple Competitive Assay to Determine Peptide Affinity for HLA Class II Molecules: A Useful Tool for Epitope Prediction; Elsevier; Journal of Immunological Methods; 2011; 9 pages; vol. 371.
Andrew J. Bordner; Towards Universal Structure-Based Prediction of Class II MHC Epitopes for Diverse Allotypes; PLoS One; 2010; 12 pages; vol. 5, No. 12.
Elena Canali et al.; A High-Performance Thioredoxin-Based Scaffold for Peptide Immunogen Construction: Proof-of-Concept Testing with a Human Papillomavirus Epitope; Scientific Reports; 2014; 11 pages; vol. 4, No. 4729.
Ethel-Michele De Villiers et al.; Classification of Papillomaviruses; Elsevier; Virology; 2004; 11 pages; vol. 324.
Da-Fei Feng et al.; Progressive Sequence Alignment as a Prerequisite to Correct Phylogenetic Trees; J. Mol. Evol.; 1987; 10 pages; vol. 25.
Ratish Gambhira et al.; A Protective and Broadly Cross-Neutralizing Epitope of Human Papillomavirus L2; Journal of Virology; Dec. 2007; 5 pages; vol. 81, No. 24.
Tzenan Giroglou et al.; Immunological Analyses of Human Papillomavirus Capsids; Elsevier, Vaccine; 2001; 11 pages; vol. 19.
Higgins et al.; Cabios; Pubmed_result.txt; 1989; 1 page; vol. 5, No. 2.
Warner K. Huh, MD et al.; The Future of Vaccines for Cervical Cancer; Gynecol Oncol.; May 2008; 17 pages; vol. 109.
Kazunari Kondo et al.; Neutralization of HPV16, 18, 31, and 58 Pseudovirions with Antisera Induced by Immunizing Rabbits with Synthetic Peptides Representing Segments of the HPV16 Minor Capsid Protein L2 Surface Region; Virology; 2007; 7 pages; vol. 358.
Nadia Moretto et al.; Conformation-sensitive Antibodies against Alzheimer Amyloid-β by Immunization with a Thioredoxin-constrained B-cell Epitope Peptide; The Journal of Biological Chemistry; Apr. 13, 2007; 11 pages; vol. 282, No. 15.
Martin Müller et al.; A Long Way: History of the Prophylactic Papillomavirus Vaccine; Disease Markers; 2007; 6 pages; vol. 23.
Saul B. Needleman et al.; A General Method Applicable to the Search for Similarities in the Amino Acid Sequence of Two Proteins; J. Mol. Biol.; 1970; 11 pages; vol. 48.

(Continued)

*Primary Examiner* — Agnieszka Boesen
(74) *Attorney, Agent, or Firm* — Taft Stettinius & Hollister LLP

(57) ABSTRACT

The present invention relates to an immunogenic polypeptide comprising (i) a B-cell epitope, (ii) a T-cell epitope, and (iii) a scaffold polypeptide, wherein said scaffold polypeptide is a thioredoxin polypeptide. The present invention further relates to said immunogenic polypeptide for use in medicine and for use in treating and/or preventing inappropriate proliferation of cells and/or infection with an infectious agent, preferably HPV infection, as well as to polypeptides and vectors encoding said immunogenic polypeptide.

14 Claims, 5 Drawing Sheets

Figure 1:
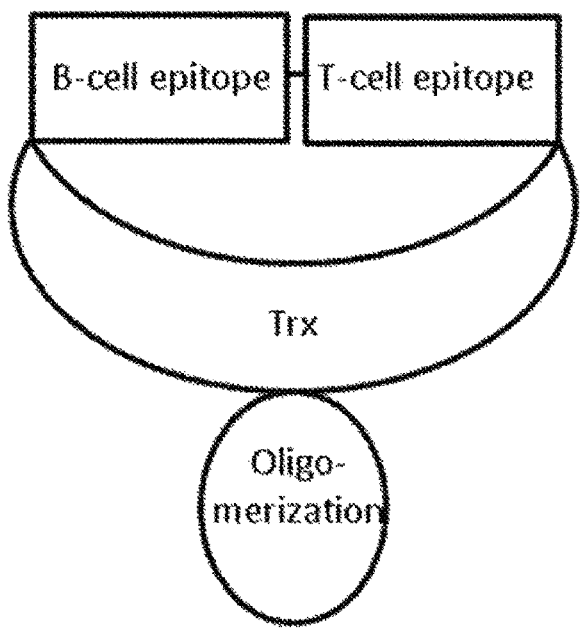

Specification includes a Sequence Listing.

(56) References Cited

OTHER PUBLICATIONS

Morten Nielsen et al.; Improved Prediction of MHC Class I and Class II Epitopes Using a Novel Gibbs Sampling Approach; Bioinformatics; 2004; 10 pages; vol. 20, No. 9.
Patricio Oyarzun et al.; Recombinant and Epitope-Based Vaccines on the Road to the Market and Implications for Vaccine Design and Production; Human Vaccines & Immunotherapeutics; 2016; 6 pages; vol. 12, No. 3.
Somayeh Pouyanfard et al.; Minor Capsid Protein L2 Polytope Induces Broad Protection Against Oncogenic and Mucosal Human Papillomaviruses; Journal of Virology; Feb. 2018; 18 pages; vol. 92, Issue 4.
Richard Roden et al.; How Will HPV Vaccines Affect Cervical Cancer ?; Nat Rev Cancer; Oct. 2006; 57 pages; vol. 6, No. 10.
Mia R. Schmiedeskamp et al.; Human Papillomavirus Vaccines; Ann Pharmacother; 2006; 9 pages; vol. 40.
Temple F. Smith et al.; Comparison of Biosequences; Advances in Applied Mathematics; 1981; 8 pages; vol. 2.
Robert W. Tindle et al.; A "Public" T-helper Epitope of the E7 Transforming Protein of Human Papillomavirus 16 Provides Cognate Help for Several E7 B-cell Epitopes from Cervical Cancer-Associated Human Papillomavirus Genotypes; Proc. Natl. Acad. Sci.; Jul. 1991; 5 pages; vol. 88.
Rongcun Yang et al.; Cell Surface-Binding Motifs of L2 That Facilitate Papillomavirus Infection; Journal of Virology; Mar. 2003; 11 pages; vol. 77, No. 6.
International Search Report; European Patent Office; International Application No. PCT/EP2019/064001; Jul. 19, 2019; 5 pages.
Written Opinion of the International Searching Authority; European Patent Office; International Application No. PCT/EP2019/064001; Jul. 19, 2019; 7 pages.

* cited by examiner

A

B

COMBINED PROPHYLACTIC AND THERAPEUTIC VACCINES

CROSS-REFERENCE TO RELATED APPLICATIONS

This application is a U.S. National Phase of International PCT Application No. PCT/EP2019/064001 filed May 29, 2019, which claims priority to European Patent Application Serial No. 18175218.9 filed May 30, 2018, the contents of each application are incorporated herein by reference in their entireties.

The present invention relates to an immunogenic polypeptide comprising (i) a B-cell epitope, (ii) a T-cell epitope, and (iii) a scaffold polypeptide, wherein said scaffold polypeptide is a thioredoxin polypeptide. The present invention further relates to said immunogenic polypeptide for use in medicine and for use in treating and/or preventing inappropriate proliferation of cells and/or infection with an infectious agent, preferably HPV infection, as well as to polypeptides and vectors encoding said immunogenic polypeptide.

Cervical cancer is women's second most frequent cancer worldwide. Clinical and molecular studies have shown that certain types of human papillomavirus (HPV), referred to as high-risk 15 types, are the etiological agents of this disease. Two anti-HPV vaccines for the prophylaxis of cervical cancer have been licensed recently by Merck (Gardasil™) and GlaxoSmithKline (Cervarix™) (Schmiedeskamp et al, (2006), Ann Pharmacother, 40: 1344-1352). Both vaccines rely on the major capsid protein L1 in the form of virus-like particles (VLPs) as antigen (Roden et al., (2006), Nat Rev Cancer, 6: 753-763); they protect against the HPV types from which the L1-VLPs were derived, yet are largely ineffective against all but the most closely related HPV types. The two most prominent high-risk HPV types, 16 and 18, are the major targets of both vaccines, although there is evidence for partial cross-protection against HPV types 31 and 45 (reviewed by Muller and Gissmann, (2007), Dis Markers, 23: 331-336; Huh and Roden, (2008), Gynecol Oncol, 109: S48-56). The limited cross-protective capacity of L1-based vaccines, which is the main reason for the continuing effort toward the development of improved vaccination strategies, likely reflects the HPV type specificity of L1 neutralizing epitopes (Giroglou et al., (2001), Vaccine, 19: 1783-1793).

Antibodies against the minor capsid protein L2 also neutralize HPV infection and are often capable to cross-neutralize various non-cognate virions, although with varying efficiencies (Kondo et al. (2007), Virology, 358: 266-272; Gambhira, R., (2007), J Virol, 81: 13927-13931). The N-terminal region of L2 interacts with an as yet unidentified secondary receptor on the surface of target cells (Yang et al. (2003), J Virol, 77: 3531-3541) and this interaction can be blocked by anti-L2 antibodies. Perhaps the most prominent N-terminal epitope is the one located between aa 17-36. This was identified as the target of an HPV16 neutralizing and protective monoclonal antibody (RG-1) as well as the major determinant of the neutralizing activity found in sera from rabbits and humans immunized with extended versions of L2 (aa 1-88, 11-200 or the full-length protein) (Gambhira, 2007, loc cit.). Since it had been found that mutation of L2 amino acids 18 and 19 or of amino acids 20 and 21 disrupted both L2 binding to the cell surface and viral infection (Yang, R., et al. (2003), J. Virol. 77: 3531-3541), it was concluded that the epitope recognized by the RG-1 antibody overlaps the surface-binding motif of HPV16 L2.

A recently developed alternative strategy for increasing peptide immunogenicity relies on the use of thioredoxin (Trx) as a scaffold protein with the ability to constrain the structure of single-copy as well as multimeric (tandemly repeated) peptide epitopes inserted within its surface-exposed active site loop (Moretto et al. (2007), J Biol Chem, 282, 11436-11445). This strategy has also been used to present HPV L2 peptides for immunization (WO 2010/070052). In a subsequent improvement of the thioredoxin scaffold, it was found that by using Trx variants from Archaebacteria, induction of anti-host thioredoxin antibodies can be significantly reduced (Canali et al. (2014), Scientific Reports 4, Art. No 4729:1).

The principal role of B-cells in the immune system is the production of antigen-specific antibodies upon their activation. Activation requires that the B-cell-receptor (BCR) on the surface of the B-cell becomes bound to its cognate antigen (B-cell epitope). This activation of the BCR leads to activation of the B-cell, which undergoes maturation and clonal expansion, after which part of the cells produced in this way becomes plasma cells producing antibodies specific for said antigen.

Another important branch of the adaptive immune system are epitope-specific T-cells. In humans, these cells have a T-cell-receptor on their surface, the recognition domain of which is specific for a defined complex between an antigenic peptide (T-cell epitope) and a major histocompatibility complex (MHC) protein. If the T-cell-receptor is engaged in a cognate interaction, the T-cell becomes activated, multiplies, and performs its activatory or inhibitory task in the immune response.

The MHC molecules come in two forms: MHC class I are expressed on the surface of every human cell and present, essentially randomly, peptides derived from proteins present in the cell's cytosol; they, thus, give a continuous overview of the protein repertoire of the cell and allow for recognition of non-normal protein expression, e.g. during viral infection of the cell or in carcinogenesis. In order to recognize MHC class I molecule—peptide complexes, the T-cell receptor requires the CD8 surface protein as a co-receptor. There is thus a subclass of T-cells expressing the CD8 co-receptor, named CD8+—T-cells; their main but not exclusive function is to eliminate body cells presenting peptides that indicate potential pathogenic processes in said cell, e.g. virus infection, which is why they are also called cytotoxic T-cells.

MHC class 11 are expressed only on professional antigen presenting cells (APCs). On these, peptides are presented that are derived from proteins that were ingested by the APCs, mainly by endocytosis. Recognition of MHC class II requires the coreceptor CD4, which is expressed only on the surface of CD4+ T-cells. The primary role of these T-cells, also called T-helper cells, is the activation of CD8+-T-cells, macrophages, and B-cells. Delivery of suitable epitopes to APCs thus leads to presentation of these epitopes via MHC class II to helper T-cells, which in turn activates these T-cells and leads to the activation of the other branches of the immune system.

There is, thus, still a need in the art for improved immunological agents for the treatment and prevention of infectious disease, such as papillomavirus infection, as well as cancer treatment and prevention. The technical problem underlying the present invention can be seen as the provision of means and methods for complying with the aforementioned needs. The technical problem is solved by the embodiments characterized in the claims and herein below.

Accordingly, the present invention relates to an immunogenic polypeptide comprising (i) a T-cell epitope, (ii) a B-cell epitope, and (iii) a scaffold polypeptide, wherein said scaffold polypeptide is a thioredoxin polypeptide.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention.

As used herein, the term "standard conditions", if not otherwise noted, relates to IUPAC standard ambient temperature and pressure (SATP) conditions, i.e. preferably, a temperature of 25° C. and an absolute pressure of 100 kPa; also preferably, standard conditions include a pH of 7. Moreover, if not otherwise indicated, the term "about" relates to the indicated value with the commonly accepted technical precision in the relevant field, preferably relates to the indicated value ±20%, more preferably ±10%, most preferably ±5%. Further, the term "essentially" indicates that deviations having influence on the indicated result or use are absent, i.e. potential deviations do not cause the indicated result to deviate by more than ±20%, more preferably ±10%, most preferably +5%. Thus, "consisting essentially of" means including the components specified but excluding other components except for materials present as impurities, unavoidable materials present as a result of processes used to provide the components, and components added for a purpose other than achieving the technical effect of the invention. For example, a composition defined using the phrase "consisting essentially of" encompasses any known acceptable additive, excipient, diluent, carrier, and the like. Preferably, a composition consisting essentially of a set of components will comprise less than 5% by weight, more preferably less than 3% by weight, even more preferably less than 1%, most preferably less than 0.1% by weight of non-specified component(s). In the context of nucleic acid sequences, the term "essentially identical" indicates a % identity value of at least 80%, preferably at least 90%, more preferably at least 98%, most preferably at least 99%. As it will be understood, the term essentially identical includes 100% identity. The aforesaid applies to the term "essentially complementary" mutatis mutandis.

The term "immunogenic polypeptide", as used herein, relates to a, preferably non-naturally occurring, polypeptide comprising the elements as specified herein. The immunogenic polypeptide referred to herein comprises at least a T-cell epitope, a B-cell epitope, and a scaffold polypeptide, all as specified elsewhere herein. As specified herein below, the immunogenic polypeptide may comprise further domains, like, preferably, immune enhancers, oligomerization domains, and the like. Preferably, said domains are linked by non-covalent bonds and have a dissociation constant of at most $10^{-6}$ mol/l, more preferably of at most $10^{-7}$ mol/l, most preferably at most $10^{-8}$ mol/l. More preferably, at least two domains are covalently connected, preferably by a peptide bond. Most preferably, all domains of the immunogenic polypeptide are covalently connected, preferably by peptide bonds; i.e. preferably, the immunogenic polypeptide is a polypeptide having a continuous chain of amino acids. Thus, preferably, the immunogenic polypeptide is encoded by a single open reading frame. Preferably, the immunogenic polypeptide has the biological function of being immunogenic, inducing a humoral and/or a cellular immune response in a subject, more preferably inducing a humoral and a cellular immune response in a subject. Most preferably, the immunogenic polypeptide has the biological function of inducing immunity to at least one, more preferably at least three, still more preferably at least eight, most preferably at least ten HPV genotypes. Preferably, in the immunogenic polypeptide, at least one of said B-cell epitope and said T-cell epitope is an epitope of a tumor antigen and/or of an antigen of an infectious agent; more preferably, both the B-cell epitope and the T-cell epitope are epitopes of a tumor antigen and/or of an antigen or of antigens of an infectious agent. Still more preferably, at least one of said B-cell epitope and said T-cell epitope is an epitope of a viral polypeptide; most preferably, both the B-cell epitope and the T-cell epitope are epitopes of viral polypeptides. Preferably, the B-cell epitope and the T-cell epitope of the immunogenic polypeptide are derived from non-identical polypeptides, more preferably are derived from non-homologous polypeptides. Preferably, the immunogenic polypeptide comprises a multitude of PV L2 N-terminal peptides corresponding to amino acids 15 to 50 of the L2 polypeptide of HPV16, as specified herein below. More preferably, said multitude is a number of from 5 to 20, preferably of from 6 to 19, most preferably of from 6 to 16 PV L2 N-terminal peptides. Also preferably, the immunogenic polypeptide comprises PV L2 N-terminal peptides from at least two, preferably at least four, more preferably at least six, most preferably all HPV genotypes selected from the list consisting of HPV 16, 18, 31, 33, 35, 6, 51, and 59. Also preferably, the immunogenic polypeptide comprises three copies, more preferably two copies, most preferably one copy of each of said PV L2 N-terminal peptides as B-cell epitopes. Preferably, the immunogenic polypeptide comprises a peptide comprising a multitude of B-cell epitopes, preferably PV L2 N-terminal peptides, as specified elsewhere herein, preferably wherein said peptide comprising a multitude of PV L2 N-terminal peptides has the amino acid sequence of SEQ ID NO:1 or a sequence at least 80% identical to SEQ ID NO:1; said peptide preferably is encoded by the nucleic sequence of SEQ ID NO:30. More preferably, the immunogenic polypeptide comprises a peptide comprising a multitude of PV L2 N-terminal peptides, wherein said peptide comprising a multitude of PV L2 N-terminal peptides has the amino acid sequence of SEQ ID NO:1. Preferably, the immunogenic polypeptide comprises a peptide comprising a multitude of T-cell epitopes, preferably E7 peptides, as specified elsewhere herein, preferably wherein said peptide comprising a multitude of E7 peptides has the amino acid sequence of SEQ ID NO:2 or a sequence at least 80% identical to SEQ ID NO:2; said peptide preferably is encoded by the nucleic sequence of SEQ ID NO:31. More preferably, the immunogenic polypeptide comprises a peptide comprising a multitude of E7 peptides, wherein said peptide comprising a multitude of E7 peptides has the amino acid sequence of SEQ ID NO:2. Preferably, the immunogenic polypeptide comprises the amino acid sequence of SEQ ID NO:1 or a sequence at least 80% identical to said sequence; and the amino acid sequence of SEQ ID NO:2, or a sequence at least 80% identical to said sequence. More preferably, the immunogenic polypeptide comprises the amino acid sequence of SEQ ID NO:3 or a sequence at least 80% identical to said sequence, in particular, comprises the amino acid sequence of SEQ ID NO:3; said peptide preferably is encoded by the nucleic sequence of SEQ ID NO:32. Still more preferably, the immunogenic polypeptide comprises the amino acid sequence of SEQ ID NO:4 or a sequence at least 80% identical to said sequence, in particular comprises the amino acid sequence of SEQ ID NO:4; said immunogenic peptide preferably is encoded by the nucleic sequence of SEQ ID NO:33. Most preferably, the immunogenic polypeptide comprises (i) the amino acid of SEQ ID NO:5; (ii) an amino acid sequence at least 70% identical to the amino acid sequence of SEQ ID NO:5; (iii) a polypeptide sequence encoded by SEQ ID NO:34 and/or (iv) a polypeptide encoded by a polynucleotide sequence at least 70% identical to the sequence of SEQ ID NO:34.

Preferably, the term immunogenic polypeptide includes variants of the specific immunogenic polypeptides described herein. As used herein, the term "polypeptide variant" relates to any chemical molecule comprising at least the polypeptides as specified herein, having the indicated activity, but differing in structure from said polypeptide indicated herein. Preferably, the polypeptide variant comprises a peptide having an amino acid sequence corresponding to an amino acid sequence of from 25 to 500, more preferably of from 30 to 300, most preferably, of from 35 to 150 consecutive amino acids comprised in a polypeptide as specified herein. Also encompassed are further polypeptide variants of the aforementioned polypeptides. Such polypeptide variants have at least the same essential biological activity as the specific polypeptides. Moreover, it is to be understood that a polypeptide variant as referred to in accordance with the present invention shall have an amino acid sequence which differs due to at least one amino acid substitution, deletion and/or addition, wherein the amino acid sequence of the variant is still, preferably, at least 50%, 60%, 70%, 80%, 85%, 90%, 92%, 95%, 97%, 98%, or 99% identical to the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the sequence it is compared to for optimal alignment. The percentage is calculated by determining, preferably over the full length of the peptide, the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981), by the homology alignment algorithm of Needleman and Wunsch (1970), by the search for similarity method of Pearson and Lipman (1988), by computerized implementations of these algorithms (GAP, BESTFIT, BLAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Polypeptide variants referred to above may be derived from allelic variants or any other species specific homologs, paralogs, or orthologs. Moreover, the polypeptide variants referred to herein include fragments of the specific polypeptides or the aforementioned types of polypeptide variants as long as these fragments and/or variants have the biological activity as referred to above. Such fragments may be or be derived from, e.g., degradation products or splice variants of the polypeptides. Further included are variants which differ due to posttranslational modifications such as phosphorylation, glycosylation, ubiquitinylation, sumoylation, or myristylation, by including non-natural amino acids, and/or by being peptidomimetics. Moreover, variants of the immunogenic polypeptide of the present invention, preferably, include variants wherein at least one domain is a variant of a domain described herein.

The term "epitope" is known to the skilled person to relate to a (sub-)structure of an antigen which is recognizable for an immune system. As used herein, the epitope is a sequence of amino acids, preferably a contiguous sequence of amino acids, i.e. a peptide. Preferably, the epitope has a length of at least three, more preferably at least four, more preferably at least five, most preferably at least six amino acids. Also preferably, the epitope has a length of at most 50, more preferably at most 25, even more preferably at most 20, most preferably at most 15 amino acids. Thus, preferably, the epitope has a length of from 3 to 50, more preferably from 4 to 25, even more preferably of from 5 to 20, most preferably of from 6 to 15 amino acids.

The term "B-cell epitope", as used herein, relates to a contiguous sequence of amino acids comprised in a peptide recognizable by antibodies of an immune system. Thus, preferably, the B-cell epitope is a peptide inducing a humoral (antibody) response in a subject. The skilled artisan knows how to predict B-cell epitopes, e.g. from Larsen et al. (2006), Immunome Research 2:2. Preferably, the B-cell epitope is an epitope derived from a tumor antigen, i.e. an amino acid sequence comprised in a protein expressed essentially only in or on an inappropriately proliferating cell, e.g. a tumor or cancer cell; thus, preferably, the B-cell epitope is an epitope essentially not or not occurring on normal cells of a subject, i.e. on non-inappropriately proliferating cells of said subject, as specified herein below. Preferably, the B-cell epitope is an epitope of a tumor antigen and/or of an antigen of an infectious agent as specified herein below. More preferably, the B-cell epitope is an epitope of an infectious agent, more preferably a viral polypeptide, most preferably a viral structural polypeptide; preferably, said viral polypeptide is a papillomavirus (PV) polypeptide, more preferably from a human PV (HPV), still more preferably a high-risk HPV genotype, most preferably a high-risk mucosal HPV genotype. Preferably, the B-cell epitope is derived from at least one of HPV genotypes selected from the list consisting of HPV 16, 18, 31, 33, 35, 6, 51, and 59. As will be understood by the skilled person, the immunogenic polypeptide may comprise more than one B-cell epitope, e.g. preferably of from 2 to 20, more preferably of from 6 to 19, most preferably of from 6 to 16 B-cell epitopes. In such case, the B-cell epitopes preferably are derived from non-identical polypeptides, more preferably from homologous polypeptides; still more preferably, the B-cell epitopes are derived from corresponding regions of homologous polypeptides in such case. Preferably, the B-cell epitope is a peptide derived from a late PV polypeptide, preferably from L1 or L2, more preferably is a PV L2 N-terminal peptide corresponding to amino acids 15 to 50 of the L2 polypeptide of HPV16 (SEQ ID NO:6) or corresponding to amino acids 65 to 89 of the L2 polypeptide of HPV16 (SEQ ID NO:7), still more preferably is a PV L2 N-terminal peptide corresponding to amino acids 20 to 38 of the L2 polypeptide of HPV16 (SEQ ID NO:8).

The term "homologous polypeptides" is understood by the skilled person to relate to polypeptides being evolutionarily related and, thus, being similar in amino acid sequence. Preferably, as used herein, the term homologous polypeptides is used for polypeptides being at least 75%, more preferably at east 80%, still more preferably at least 85%, even more preferably at least 90%, most preferably at least 95% identical in amino acid sequence, preferably determined as specified herein above, more preferably irrespective of their evolutionary relationship.

The term "T-cell epitope", as used herein, relates to a contiguous sequence of amino acids comprised in a peptide, which can be bound to a major histocompatibility complex (MHC) class I or class II molecule to be presented on the surface of a cell (MHC-I) or of a professional antigen presenting cell (MHC-II). The skilled artisan knows how to predict immunogenic peptides presented on MHC-I or MHC-II (Nielsen et al., (2004), Bioinformatics, 20 (9), 1388-1397), Bordner (2010), PLoS ONE 5(12): e14383) and how to evaluate binding of specific peptides (e.g. Bernardeau et al., (2011), J Immunol Methods, 371(1-2):97-105). Preferably, the T-cell epitope is an MHC-I epitope. Preferably, the T-cell epitope is an epitope derived from a tumor antigen, i.e. an amino acid sequence comprised in a protein expressed essentially only in or on an inappropriately proliferating cell, e.g. a tumor or cancer cell; thus, preferably, the T-cell epitope is an epitope essentially not or not occurring on normal cells of a subject, i.e. on non-inappropriately proliferating cells of said subject. Preferably, the T-cell epitope is an epitope of a tumor antigen and/or of an antigen of an infectious agent as specified herein below. More preferably, the T-cell epitope is an epitope of an infectious agent, in particular a viral polypeptide, more preferably of a papillomavirus (PV) polypeptide, even more preferably from a human PV (HPV), preferably high-risk HPV genotype, more preferably a high-risk mucosal HPV genotype. Preferably, the T-cell epitope is derived from at least one of HPV genotypes selected from the list consisting of HPV 16, 18, 31, 33, 35, 6, 51, and 59. Preferably, the T-cell epitope is a peptide derived from an early gene of a PV, more preferably from an E6 or E7 polypeptide, most preferably from an E7 polypeptide. Preferably, the T-cell epitope has an amino acid sequence corresponding to the amino acid sequence of amino acids 49 to 57 of HPV16 E7, more preferably said T-cell epitope has the amino acid sequence RAHYNIVTF (SEQ ID NO:9). Preferably, the T-cell epitope is flanked N-terminally and/or C-terminally by at least 3, preferably at least 4, more preferably at least 5 amino acids; more preferably, the amino acid sequence of the N-terminally flanking sequence is QAEPD (SEQ ID NO:10) and/or the amino acid sequence of the C-terminally flanking sequence is CCKCD (SEQ ID NO:11). Thus, preferably, the amino acid sequence of the N-terminally and C-terminally flanked T-cell epitope is QAEPDRAHYNIVTFCCKCD (SEQ ID NO:12). As will be understood by the skilled person, the immunogenic polypeptide may comprise more than one T-cell epitope, e.g. preferably of from 2 to 15, more preferably of from 2 to 10, even more preferably of from 2 to 8 T-cell epitopes, most preferably 3 T-cell epitopes. In such case, the T-cell epitopes preferably are MHC-I and MHC-II epitopes; more preferably, the T-cell epitopes are epitopes presented by MHCs of different genes. More preferably, the T-cell epitopes are epitopes presented by different MHC alleles and/or subtypes. Preferably, all T-cell epitopes comprised in the immunogenic polypeptide are derived from homologous polypeptides. More preferably, all T-cell epitopes comprised in the immunogenic polypeptide are derived from the same polypeptide, even more preferably comprise identical T-cell epitopes, most preferably are identical T-cell epitopes.

The term "scaffold polypeptide" is known to the skilled person and includes all polypeptides providing a backbone for attachment, preferably covalent attachment, of the epitopes of the immunogenic polypeptide. Preferably, the scaffold polypeptide is a globular polypeptide. Also preferably, the scaffold polypeptide, in its native state, i.e. without association of the epitopes as specified herein, is a monomeric or oligomeric polypeptide. In case the scaffold polypeptide is an oligomeric polypeptide, it preferably is a homo-oligomer. More preferably, the scaffold polypeptide, in its native state, is a monomeric polypeptide. The epitopes may, in principle, be attached N-terminally, C-terminally, and/or within the scaffold polypeptide.

As used herein, the scaffold polypeptide is a thioredoxin. The term "thioredoxin" is known to the skilled person to relate to a family of small redox polypeptides conserved essentially over all living organisms. Preferably, the thioredoxin is a mammalian, more preferably human, a bacterial, or an archaebacterial thioredoxin. More preferably, the thioredoxin is an archaebacterial thioredoxin, preferably from a thermophilic archaebacterium (archeon), preferably of *Pyrococcus furiosus* or of *Methanosaeta thermophila*. Thus, the thioredoxin preferably has the amino acid sequence of SEQ ID NO: 13 (human thioredoxin), preferably encoded by the nucleic acid sequence of SEQ ID NO: 14, or is a variant thereof; or has the amino acid sequence of SEQ ID NO: 15 (mouse thioredoxin), preferably encoded by the nucleic acid sequence of SEQ ID NO: 16, or is a variant thereof; or has the amino acid sequence of SEQ ID NO: 17 (*E. coli* thioredoxin), preferably encoded by the nucleic acid sequence of SEQ ID NO: 18, or is a variant thereof. More preferably, the thioredoxin has the amino acid sequence of SEQ ID NO: 19 (*P. furiosus* thioredoxin), preferably encoded by the nucleic acid sequence of SEQ ID NO: 20, or is a variant thereof; or has the amino acid sequence of SEQ ID NO: 21 (*M. thermophila* thioredoxin), preferably encoded by the nucleic acid sequence of SEQ ID NO: 22, or is a variant thereof. Suitable thioredoxin polypeptides are in particular known from WO 2010/070052. As will be understood by the skilled person, the thioredoxins of the present invention have the biological activity of being a scaffold, whereas their redox-activity is not required. Accordingly, according to the present invention, variant thioredoxins with a sequence identity of at least 50% to one of the aforesaid thioredoxins are suitable for use in the immunogenic polypeptide. Preferably, the multitude of L2 N-terminal peptides is inserted into the "display site" of the thioredoxin, as described in detail in WO 2010/070052.

The terms "linker" and "linker peptide" are in principle known to the skilled person. The person skilled in the art knows how to select suitable linker peptides. Preferably, the linker comprises 1 to 5 amino acids, which are preferably selected from the group consisting of Glycine (G), Proline (P) or Serine (S). A particularly preferred linker peptide comprises the amino acid sequence GGP (SEQ ID NO: 23). However, also other linkers can be used such as GP (SEQ ID NO:24), GS (SEQ ID NO:25), GPGP (SEQ ID NO:26), GPGPG (SEQ ID NO: 27), or SGSG (SEQ ID NO: 28). Preferably, said linker peptide is positioned at the junction of the scaffold polypeptide, i.e. the thioredoxin polypeptide as described elsewhere herein, and the B-cell epitope and/or the T-cell epitope. Also preferably, an independently selected linker may intervene between the B-cell epitope and the T-cell epitope. Also preferably, in case more than one B-cell epitope and/or T-cell epitope is or are present in the immunogenic polypeptide, independently selected linkers may also intervene said B-cell epitopes and/or T-cell epitopes.

As used herein, the term "papillomavirus" (PV) relates to a DNA virus from the papillomaviridae family of viruses that infects the skin and mucous membranes of mammals, preferably livestock, more preferably cattle and horses, most preferably humans. For human PV (HPV), more than 110 HPV genotypes have been described (de Villiers, E. M., C. Fauquet, T. R. Broker, H. U. Bernard, and H. zur Hausen. 2004. Classification of papillomaviruses. Virology 324:17-27). Approximately 50 HPV genotypes are known to infect the mucosa. These mucosal genotypes are classified into three different groups based on their epidemiological association with cancer: "low-risk" human papillomaviruses (LR-HPV), "high-risk" human papillomaviruses (HR-HPV) and "putative high-risk" human papillomaviruses (pHR-HPV). It is also known that HR-HPVs can cause vulvar, anal, vaginal, penile, and oropharyngeal cancer, as well as vaginal intraepithelial neoplasia, anal intraepithelial neoplasia, vulvar intraepithelial neoplasia, and penile intraepithelial neoplasia. Preferably, HPVs are mucosal HPVs; more preferably, HPVs of the current invention are High-risk HPV genotypes (HR-HPVs), which are the main cause for the development of cervical cancer. Preferably, HPVs are HPV 31, 33, 35, 39, 45, 51, 52, 56, 58, 59, 68, 73 and 82, more preferably HPV 6, 16, 18, 31, 33, 35, 39, 45, 51, 56, 59 and 82, most preferably HPV 6, 16, 18, 31, 33, 35, 51 and 59.

The term "inappropriate cellular proliferation" relates to an abnormal proliferation of body cells in a subject; as a consequence, an imbalance of cellular composition of a body tissue, of a body fluid and/or tumor formation may ensue. Inappropriate cellular proliferation may be induced by an infectious agent, preferably a virus, more preferably an oncogenic virus, more preferably a papillomavirus, Epstein-Barr virus, a hepatitis virus, Human T-lymphotropic virus 1, Human herpesvirus 8, more preferably a papillomavirus (PV), most preferably a human papillomavirus (HPV). Inappropriate cellular proliferations may, however, also be induced by chemical compounds, e.g. a carcinogen, or endogenously, e.g. caused by spontaneous mutation. Preferably, inappropriate cellular proliferation is benign, i.e. preferably, does not threaten health or life of a subject. Preferred benign inappropriate cellular proliferations are warts, exophytic growing papillomas, condylomata, inverted papillomas, and pre-neoplastic HPV-induced lesions. More preferably, inappropriate cellular proliferation is malignant, i.e. does threaten health or life of a subject; thus, preferably, the malignant inappropriate cellular proliferation is cancer. The term "cancer", as used herein, relates to a disease of an animal, including man, characterized by uncontrolled growth by a group of body cells ("cancer cells"). This uncontrolled growth may be accompanied by intrusion into and destruction of surrounding tissue and possibly spread of cancer cells to other locations in the body. Preferably, also included by the term cancer is a relapse. Thus, preferably, the cancer is a solid cancer, a metastasis, or a relapse thereof.

Preferably, the cancer is selected from the list consisting of acute lymphoblastic leukemia, acute myeloid leukemia, adrenocortical carcinoma, aids-related lymphoma, anal cancer, appendix cancer, astrocytoma, atypical teratoid, basal cell carcinoma, bile duct cancer, bladder cancer, brain stem glioma, breast cancer, burkitt lymphoma, carcinoid tumor, cerebellar astrocytoma, cervical cancer, chordoma, chronic lymphocytic leukemia, chronic myclogenous leukemia, colon cancer, colorectal cancer, craniopharyngioma, endometrial cancer, ependymoblastoma, ependymoma, esophageal cancer, extracranial germ cell tumor, extragonadal germ cell tumor, extrahepatic bile duct cancer, fibrosarcoma, gallbladder cancer, gastric cancer, gastrointestinal stromal tumor, gestational trophoblastic tumor, hairy cell leukemia, head and neck cancer, hepatocellular cancer, hodgkin lymphoma, hypopharyngeal cancer, hypothalamic and visual pathway glioma, intraocular melanoma, kaposi sarcoma, laryngeal cancer, medulloblastoma, medulloepithelioma, melanoma, merkel cell carcinoma, mesothelioma, mouth cancer, multiple endocrine neoplasia syndrome, multiple myeloma, mycosis fungoides, nasal cavity and paranasal sinus cancer, nasopharyngeal cancer, neuroblastoma, non-hodgkin lymphoma, non-small cell lung cancer, oral cancer, oropharyngeal cancer, osteosarcoma, ovarian cancer, ovarian epithelial cancer, ovarian germ cell tumor, ovarian low malignant potential tumor, pancreatic cancer, papillomatosis, paranasal sinus and nasal cavity cancer, parathyroid cancer, penile cancer, pharyngeal cancer, pheochromocytoma, pituitary tumor, pleuropulmonary blastoma, primary central nervous system lymphoma, prostate cancer, rectal cancer, renal cell cancer, retinoblastoma, rhabdomyosarcoma, salivary gland cancer, sézary syndrome, small cell lung cancer, small intestine cancer, soft tissue sarcoma, squamous cell carcinoma, squamous neck cancer, testicular cancer, throat cancer, thymic carcinoma, thymoma, thyroid cancer, urethral cancer, uterine sarcoma, vaginal cancer, vulvar cancer, waldenström macroglobulinemia, and wilms tumor. More preferably, the cancer is a solid cancer, a metastasis, or a relapse thereof. Most preferably, the cancer is a tumor of a HPV-positive cancer, preferably HPV-positive head and neck cancer and/or cervix carcinoma. Thus, preferably, the cancer cells are papillomavirus-positive cancer cells, preferably are human papillomavirus-positive cancer cells.

The term "tumor antigen", as used herein, relates to any antigenic compound, preferably a polypeptide or epitope thereof, detectable in an inappropriately proliferating cell, but not or to an at least 5fold, preferably at least 10fold, lower extent in normal body cells, in particular surrounding cells of the same tissue. Thus, preferably, the tumor antigen is specific for an inappropriately proliferating cell, preferably as compared to the remaining cells of the subject comprising said inappropriately proliferating cell. Preferably, the tumor antigen is an antigen specific for a tumor cell, preferably for a PV-associated benign lesion and/or for a cancer cell as specified herein above.

The term "subject", as used herein, relates to an animal, preferably a vertebrate, more preferably a mammal, in particular to livestock like cattle, horse, pig, sheep, and goat, or to a laboratory animal like a rat, mouse, and guinea pig. Most preferably, the subject is a human.

The term "infectious agent", as used herein, relates to an agent, preferably a microorganism, causing transmissible disease in a subject. Preferably, the infectious agent is a bacterium, an eukaryotic infectious agent, e.g. a *Plasmodium* spp. or a virus, more preferably is a virus, e.g. a Papillomavirus, a Hepatitis virus or Human Immunodeficiency Virus (HIV). more preferably, the infectious agent is an oncogenic virus, more preferably a Papillomavirus, Epstein-Barr virus, a hepatitis virus, Human T-lymphotropic virus 1, Human herpesvirus 8, more preferably a papillomavirus (PV), most preferably a human papillomavirus (HPV). Preferably, the infectious agent is an agent causing chronic disease. More preferably, the infectious agent is an agent causing chronic and/or persisting infection.

Preferably, the immunogenic polypeptide further comprises an oligomerization domain. The term "oligomerization domain" is used in its conventional meaning and relates to a polypeptide having the property that polypeptides comprising said domain have a propensity to aggregate. Preferably, the dissociation constant for the oligomerization domain as a separate molecule is at most $10^{-4}$ mol/l, more preferably at most $10^{-5}$ mol/1, most preferably at least $10^{-6}$ mol/l. As will be appreciated, the number of molecules aggregating will in particular depend on the type of oligomerization domain selected. Suitable oligomerization domains are known in the art. Preferably, the immunogenic polypeptide comprises at least one oligomerization domain of (i) an oligomerization domain of a C4-binding protein, preferably of a mammalian C4-binding protein, more preferably of a human or mouse C4-binding protein, most preferably of a mouse C4-binding protein; (ii) an encapsulin polypeptide, preferably an encapsulin polypeptide from a thermophilic archaebacterium, more preferably a *Pyrococcus furiosus* encapsulin polypeptide; (iii) a ferritin polypeptide, preferably a ferritin polypeptide from a thermophilic archaebacterium, more preferably a *Pyrococcus furiosus* ferritin polypeptide; and (iv) a hybrid polypeptide of two different chicken C4-binding proteins, preferably an IMX313 polypeptide or a variant thereof, in particular as described in WO 2007/062819 A2, most preferably an IMX313T polypeptide (SEQ ID NO:29). The IMX313T polypeptide has also been referred to as "OVX313 domain".

Advantageously, it was found in the work underlying the present invention that by combining T-cell epitopes and B-cell epitopes in an immunogenic polypeptide with thioredoxin as a scaffold, not only a robust antibody response to the B-cell antigen, but also an improved T-cell response to the T-cell antigen can be induced. Thus, the immunogenic polypeptide disclosed can be used to clear persistent infection in a subject and at the same time vaccinate said subject against fresh infection.

The definitions made above apply mutatis mutandis to the following. Additional definitions and explanations made further below also apply for all embodiments described in this specification mutatis mutandis.

The present invention further relates to the immunogenic polypeptide of the present invention for use in medicine, and to the immunogenic polypeptide of the present invention for use in treating and/or preventing inappropriate proliferation of cells and/or infection with an infectious agent, preferably HPV infection.

The terms "treating" and "treatment" refer to an amelioration of the diseases or disorders referred to herein or the symptoms accompanied therewith to a significant extent. Said treating as used herein also includes an entire restoration of health with respect to the diseases or disorders referred to herein. It is to be understood that treating, as the term is used herein, may not be effective in all subjects to be treated. However, the term shall require that, preferably, a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 10%, at least 20% at least 50% at least 60%, at least 70%, at least 80%, or at least 90% of the subjects of a given cohort or population. Preferably, treating cancer is reducing tumor burden in a subject. As will be understood by the skilled person, effectiveness of treatment of e.g. cancer is dependent on a variety of factors including, e.g. cancer stage and cancer type. Preferably, treating causes inappropriately proliferating cells, preferably neoplastic cells, more preferably cancer cells, to be recognized by T-cells of the subject. Thus, preferably, treating has the effect of causing a tumor to stop growing, more preferably to cause regression of a tumor, more preferably of causing a tumor to resolve. As used herein, the above relates to treating a HPV-related lesion mutatis mutandis.

The term "preventing" refers to retaining health with respect to the diseases or disorders referred to herein for a certain period of time in a subject. It will be understood that the said period of time may be dependent on the amount of the drug compound which has been administered and individual factors of the subject discussed elsewhere in this specification. It is to be understood that prevention may not be effective in all subjects treated with the compound according to the present invention. However, the term requires that, preferably, a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well known statistic evaluation tools discussed elsewhere in this specification. Thus, preferably, in case of disease caused by an infectious agent, preventing may be vaccination. Thus, preferably, the term preventing relates to administering the compounds as specified herein to elicit an immune response against at least one infectious agent. Thus, vaccination stimulates the immune system and establishes or improves immunity to infection with infectious agents. Preferably, vaccination according to the present invention allows for establishing or improving immunity to infection with infectious agent, preferably human papillomavirus genotypes. It is to be understood that the vaccine according to the present invention may comprise further components, in particular as specified elsewhere herein. The skilled person will understand that vaccination may not elicit a significant immune response in all subjects vaccinated. Also, it is to be understood that vaccination may not be effective to prevent infection in all subjects vaccinated. However, the term requires that a, preferably statistically significant, portion of subjects of a cohort or population are effectively vaccinated. In case the infectious agent is a HPV, effective vaccination, preferably, is prevention or reduction of the number of HPV-induced lesions, such as warts.

The present invention also relates to a polynucleotide encoding the immunogenic polypeptide according to the present invention.

As used herein, the term polynucleotide, preferably, includes variants of the specifically indicated polynucleotides. More preferably, the term polynucleotide relates to the specific polynucleotides indicated. It is to be understood, however, that a polypeptide having a specific amino acid sequence may be also encoded by a variety of polynucleotides, due to the degeneration of the genetic code. The skilled person knows how to select a polynucleotide encoding a polypeptide having a specific amino acid sequence and also knows how to optimize the codons used in the polynucleotide according to the codon usage of the organism used for expressing said polynucleotide. Thus, the term "polynucleotide variant", as used herein, relates to a variant of a polynucleotide related to herein comprising a nucleic acid sequence characterized in that the sequence can be derived from the aforementioned specific nucleic acid sequence by at least one nucleotide substitution, addition and/or deletion, wherein the polynucleotide variant shall have the activity as specified for the specific polynucleotide, i.e. shall encode an immunogenic polypeptide according to the present invention. Moreover, it is to be understood that a polynucleotide variant as referred to in accordance with the present invention shall have a nucleic acid sequence which differs due to at least one nucleotide substitution, deletion and/or addition. Preferably, said polynucleotide variant is an ortholog, a paralog or another homolog of the specific polynucleotide. Also preferably, said polynucleotide variant is a naturally occurring allele of the specific polynucleotide. Polynucleotide variants also encompass polynucleotides comprising a nucleic acid sequence which is capable of hybridizing to the aforementioned specific polynucleotides, preferably, under stringent hybridization conditions. These stringent conditions are known to the skilled worker and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.10% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1× to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of a polypeptide of the present invention. Conserved domains of a polypeptide may be identified by a sequence comparison of the nucleic acid sequence of the polynucleotide or the amino acid sequence of the polypeptide of the present invention with sequences of other organisms. As a template, DNA or cDNA from bacteria, fungi, plants or, preferably, from animals may be used. Further, variants include polynucleotides comprising nucleic acid sequences which are at least 70%, at least 75%, at least 80%, at least 85%, at least 90%, at least 95%, at least 98% or at least 99% identical to the specifically indicated nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences specifically indicated. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit Needleman and Wunsch (J. Mol. Biol. 48; 443-453 (1970)) and Smith and Waterman (Adv. Appl. Math. 2; 482-489 (1981))], which are part of the GCG software packet (Genetics Computer Group, 575 Science Drive, Madison, Wisconsin, USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the specifically indicated nucleic acid sequences is also encompassed as a variant polynucleotide of the present invention. The fragment shall still encode an immunogenic polypeptide which still has the activity as specified. Accordingly, the immunogenic polypeptide encoded may comprise or consist of the domains of the immunogenic polypeptide of the present invention conferring the said biological activity. A fragment as meant herein, preferably, comprises at least 50, at least 100, at least 250 or at least 500 consecutive nucleotides of any one of the specific nucleic acid sequences or encodes an amino acid sequence comprising at least 20, at least 30, at least 50, at least 80, at least 100 or at least 150 consecutive amino acids of any one of the specific amino acid sequences.

The polynucleotides of the present invention either consist, essentially consist of, or comprise the aforementioned nucleic acid sequences. Thus, they may contain further nucleic acid sequences as well. Specifically, the polynucleotides of the present invention may encode fusion proteins wherein one partner of the fusion protein is an immunogenic polypeptide being encoded by a nucleic acid sequence recited above. Such fusion proteins may comprise as additional part polypeptides for monitoring expression (e.g., green, yellow, blue or red fluorescent proteins, alkaline phosphatase and the like), so called "tags" which may serve as a detectable marker or as an auxiliary measure for purification purposes, and/or scaffold polypeptides such as thioredoxin, as described herein above. Tags for the different purposes are well known in the art and are described elsewhere herein.

The polynucleotide of the present invention shall be provided, preferably, either as an isolated polynucleotide (i.e. isolated from its natural context) or in genetically modified form. The polynucleotide, preferably, is DNA, including cDNA, or is RNA. The term encompasses single as well as double stranded polynucleotides. Moreover, preferably, comprised are also chemically modified polynucleotides including naturally occurring modified polynucleotides such as glycosylated or methylated polynucleotides or artificially modified ones such as biotinylated polynucleotides.

Furthermore, the present invention relates to a vector comprising the polynucleotide according to the present invention.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerenes. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. In a preferred embodiment, the vector is a bacterial vector, preferably having a p15A origin of replication and/or carrying a kanamycin resistance gene.

More preferably, in the vector of the invention the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). In a preferred embodiment, the vector is a bacterial expression vector carrying the nucleic acid sequence encoding the immunogenic polypeptide under the control of an inducible promoter, preferably the tac promoter; also preferably, said vector additionally carries a gene encoding an expressible gene encoding a functional lac inhibitor. Thus, in a preferred embodiment, the vector is a bacterial expression vector, preferably having a p15A origin of replication, carrying a kanamycin resistance gene, a gene encoding an expressible gene encoding a functional lac inhibitor, and encoding the immunogenic polypeptide under the control of the tac promoter.

The present invention also relates to a host cell comprising the polynucleotide according to the present invention and/or the vector according to the present invention.

As used herein, the term "host cell" relates to any cell capable of receiving and, preferably maintaining, the polynucleotide and/or the vector of the present invention. More preferably, the host cell is capable of expressing an immunogenic polypeptide of the present invention encoded on said polynucleotide and/or vector. Preferably, the cell is a bacterial cell, more preferably a cell of a common laboratory bacterial strain known in the art, most preferably an *Escherichia* strain, in particular an *E. coli* strain. Also preferably, the host cell is an eukaryotic cell, preferably a yeast cell, e.g. a cell of a strain of baker's yeast, or is an animal cell. More preferably, the host cell is an insect cell or a mammalian cell, in particular a mouse or rat cell. Most preferably, the host cell is a mammalian cell.

The present invention further relates to a pharmaceutical composition comprising the immunogenic polypeptide according to the present invention, the polynucleotide according the present invention, the vector according the present invention, and/or the host cell according to the present invention; and a pharmaceutically acceptable carrier.

The term "pharmaceutical composition", as used herein, relates to a composition comprising the compound or compounds of the present invention in a pharmaceutically acceptable form and a pharmaceutically acceptable carrier.

The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, or parenteral administration as well as inhalation. Preferably, the pharmaceutical composition of the present invention is administered via a parenteral route, preferably subcutaneously, intramuscularly, or intraperitoneally. In case the subject is a human, administration preferably is intramuscularly. However, polynucleotide compounds may also be administered in a gene therapy approach by using viral vectors, viruses or liposomes, and may also be administered topically, e.g. as an ointment. Moreover, the compounds can be administered in combination with other drugs either in a common pharmaceutical composition or as separated pharmaceutical compositions wherein said separated pharmaceutical compositions may be provided in form of a kit of parts. In particular, co-administration of adjuvants is envisaged, as specified elsewhere herein. Preferably, the immunogenic polypeptide, the polynucleotide and the pharmaceutical composition are provided in lyophilized form.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pennsylvania.

The diluent(s) is/are preferably selected so as not to affect the biological activity of the immunogenic polypeptide, polynucleotide, vector, or host cell and potential further pharmaceutically active ingredients. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats a condition referred to herein. Therapeutic efficacy and toxicity of compounds can be determined by standard pharmaceutical procedures in cell culture or in experimental animals, e.g., by determining the ED50 (the dose therapeutically effective in 50% of the population) and/or the LD50 (the dose lethal to 50% of the population). The dose ratio between therapeutic and toxic effects is the therapeutic index, and it can be expressed as the ratio, LD50/ED50.

The dosage regimen will be determined by the attending physician, preferably taking into account relevant clinical factors and, preferably, in accordance with any one of the methods described elsewhere herein. As is well known in the medical arts, a dosage for any one patient may depend upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 μg to 10000 μg; however, doses below or above this exemplary range are envisioned, especially considering the aforementioned factors. Generally, the regimen comprises administration of 1 μg to 10 mg of an antigen as a primary immunization, followed by one or more than one boost administration of the same antigen, preferably in the same dosage. However, depending on the subject and the mode of administration, the quantity of substance administration may vary over a wide range to provide from about 0.01 mg per kg body mass to about 1 mg per kg body mass, preferably. The pharmaceutical compositions and formulations referred to herein are administered at least once in order to treat or prevent a disease or condition recited in this specification. However, the said pharmaceutical compositions may be administered more than one time, for example, preferably from one to four times, more preferably two or three times.

Specific pharmaceutical compositions are prepared in a manner well known in the pharmaceutical art and comprise at least an immunogenic polypeptide, polynucleotide, vector, or host cell as an active compound in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescriber or user instructions in order to anticipate dose adjustments depending on the considered recipient.

The present invention further relates to a kit comprising an immunogenic polypeptide according to the present invention, a polynucleotide according to the present invention, a vector according to the present invention, and/or a host cell according to the present invention comprised in a housing.

The term "kit", as used herein, refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention, preferably, is to be used for practicing the methods referred to herein above. It is, preferably, envisaged that all components are provided in a ready-to-use manner for practicing the methods referred to above. Further, the kit, preferably, contains instructions for carrying out said methods. The instructions can be provided by a user's manual in paper or electronic form. In addition, the manual may comprise instructions for administration and/or dosage instructions for carrying out the aforementioned methods using the kit of the present invention. As will be understood from the above, the description of the kit comprising polynucleotides, preferably, relates to a kit comprising corresponding vectors mutatis mutandis.

Preferably, the kit comprises the immunogenic polypeptide according to the present invention and an adjuvant. The term "adjuvant" is used herein in its usual meaning in the art. Preferably, the adjuvant comprises (i) alum and a toll like receptor 4 (TLR4) agonist, preferably synthetic monophosphoryl lipid A (MPLA), and/or (ii) a squalene-based oil-in-water nano-emulsion, preferably AddaVax™. Also preferably, the kit comprises a diluent and/or a means of administration. Appropriate diluents are described herein above. Means of administration are all means suitable for administering the immunogenic polypeptide, the polynucleotide, the vector, and/or the host cell to a subject. The means of administration may include a delivery unit for the administration of the compound or composition and a storage unit for storing said compound or composition until administration. However, it is also contemplated that the means of the current invention may appear as separate devices in such an embodiment and are, preferably, packaged together in said kit. Preferred means for administration are those which can be applied without the particular knowledge of a specialized technician. In a preferred embodiment, the means for administration is a syringe, more preferably with a needle, comprising the compound or composition of the invention. In another preferred embodiment, the means for administration is an intravenous infusion (IV) equipment comprising the compound or composition. In still another preferred embodiment the means for administration is an inhaler comprising the compound of the present invention, wherein, more preferably, said compound is formulated for administration as an aerosol.

The present invention further relates to a pharmaceutical composition comprising the immunogenic polypeptide according to the present invention, the polynucleotide according the present invention, the vector according the present invention, and/or the host cell according to the present invention for use in medicine and for use in treating and/or preventing inappropriate proliferation of cells and/or infection with an infectious agent, preferably HPV infection.

The present invention further relates to a method of treating and/or preventing inappropriate proliferation of cells and/or infection with an infectious agent, preferably HPV infection, comprising contacting a subject with the immunogenic polypeptide according to the present invention, the polynucleotide according to the present invention, the vector according to the present invention, and/or the pharmaceutical composition according to the present invention and, thereby, treating and/or preventing HPV infection.

The method of treating and/or preventing of the present invention, preferably, is an in vivo method. Moreover, it may comprise steps in addition to those explicitly mentioned above. For example, further steps may relate, e.g., to diagnosing inappropriate proliferation of cells and/or infection with an infectious agent, before the contacting step and/or further treatment steps, such as surgery, irradiation, and/or further pharmacological treatment. Moreover, one or more of said steps may be performed by automated equipment.

Preferably, the subject to which the method is administered is suffering from at least one PV-related lesion. Also preferably, said subject is a subject at risk of becoming infected with a PV, more preferably said subject is a human at an age of at most 16 years, even more preferably at most 15 years, still more preferably at most 14 years, still more preferably at most 13 years, most preferably at most 12 years. It is, however, also envisaged that the method is administered to a subject for which the PV infection status is unknown.

The present invention furthermore relates to a composition comprising an anti-PV antibody and/or anti-PV T-cells produced or producible by contacting a subject with the immunogenic polypeptide according to the present invention, the polynucleotide according to the present invention, the vector according to the present invention, and/or the pharmaceutical composition according to the present invention, preferably wherein said subject is non-human.

The production method of the present invention, preferably, is an in vivo method. Moreover, it may comprise steps in addition to those explicitly mentioned above. Moreover, one or more of said steps may be performed by automated equipment. Preferably, the subject suitable for use in the production method is an experimental animal, preferably a mouse, rat, guinea pig, rabbit, sheep, goat, llama, donkey, or horse. In an embodiment, the subject is a human.

In view of the above, the following embodiments are preferred:

1. An immunogenic polypeptide comprising (i) a B-cell epitope, (ii) a T-cell epitope, and (iii) a scaffold polypeptide, wherein said scaffold polypeptide is a thioredoxin polypeptide.
2. The immunogenic polypeptide of embodiment 1, wherein at least one of said B-cell epitope and said T-cell epitope is an epitope of an antigen of an infectious agent and/or of a tumor antigen, preferably wherein both the B-cell epitope and the T-cell epitope are epitopes of a tumor antigen and/or of an antigen of an infectious agent.
3. The immunogenic polypeptide of embodiment 1 or 2, wherein at least one of said B-cell epitope and said T-cell epitope is an epitope of a viral polypeptide, preferably wherein both the B-cell epitope and the T-cell epitope are epitopes of viral polypeptides.
4. The immunogenic polypeptide of any one of embodiments 1 to 3, wherein at least one of said B-cell epitope and said T-cell epitope is an epitope of a papillomavirus (PV) polypeptide, preferably wherein both the B-cell epitope and the T-cell epitope are epitopes of a PV polypeptide.
5. The immunogenic polypeptide of any one of embodiments 1 to 4, wherein said B-cell epitope and said T-cell epitope are derived from non-identical polypeptides, more preferably are derived from non-homologous polypeptides.
6. The immunogenic polypeptide of any one of embodiments 1 to 5, wherein all B-cell epitopes comprised in said immunogenic polypeptide are derived from homologous polypeptides, and/or wherein all T-cell epitopes comprised in said immunogenic polypeptide are derived from homologous polypeptides.
7. The immunogenic polypeptide of any one of embodiments 1 to 6, wherein said B-cell epitope and/or said T-cell epitope are derived from a human PV (HPV), preferably high-risk HPV genotype, more preferably a high-risk mucosal HPV genotype.
8. The immunogenic polypeptide of any one of embodiments 1 to 7, wherein said B-cell epitope and/or said T-cell epitope are derived from at least one of HPV genotypes selected from the list consisting of HPV 16, 18, 31, 33, 35, 6, 51, and 59.
9. The immunogenic polypeptide of any one of embodiments 1 to 8, wherein said T-cell epitope is a peptide derived from an early gene of a PV.

10. The immunogenic polypeptide of any one of embodiments 1 to 9, wherein said T-cell epitope is a peptide derived from an E6 or E7 polypeptide, preferably from an E7 polypeptide.
11. The immunogenic polypeptide of any one of embodiments 1 to 10, wherein said T-cell epitope has an amino acid sequence corresponding to the amino acid sequence of amino acids 49 to 57 of HPV16 E7.
12. The immunogenic polypeptide of any one of embodiments 1 to 11, wherein said T-cell epitope has the amino acid sequence RAHYNIVTF (SEQ ID NO:9).
13. The immunogenic polypeptide of any one of embodiments 1 to 12, wherein said T-cell epitope is flanked N-terminally and/or C-terminally by at least 3, preferably at least 4, more preferably at least 5 amino acids.
14. The immunogenic polypeptide of embodiment 13, wherein the amino acid sequence of the N-terminally flanking sequence is QAEPD (SEQ ID NO:10) and/or the amino acid sequence of the C-terminally flanking sequence is CCKCD (SEQ ID NO:11).
15. The immunogenic polypeptide embodiment 13 or 14, wherein the amino acid sequence of the N-terminally and C-terminally flanked T-cell epitope is QAEPDRAHYNIVTFCCKCD (SEQ ID NO:12).
16. The immunogenic polypeptide of any one of embodiments 1 to 15, wherein said B-cell epitope is a peptide derived from a late PV polypeptide, preferably from L1 or L2.
17. The immunogenic polypeptide of any one of embodiments 1 to 16, wherein said B-cell epitope is a PV L2 N-terminal peptide corresponding to amino acids 15 to 50 of the L2 polypeptide of HPV16.
18. The immunogenic polypeptide of embodiment 17, wherein said PV L2 N-terminal peptides are peptides corresponding to amino acids 20 to 38 of the L2 polypeptide of HPV16.
19. The immunogenic polypeptide of any one of embodiments 1 to 18, wherein said immunogenic polypeptide comprises a multitude of PV L2 N-terminal peptides corresponding to amino acids 15 to 50 of the L2 polypeptide of HPV16.
20. The immunogenic polypeptide of any one of embodiments 1 to 19, wherein said multitude is a number of from 5 to 20, preferably of from 6 to 19, most preferably of from 6 to 16 PV L2 N-terminal peptides.
21. The immunogenic polypeptide of any one of embodiments 1 to 20, wherein said immunogenic polypeptide comprises PV L2 N-terminal peptides from at least two, preferably at least four, more preferably at least six, most preferably all HPV genotypes selected from the list consisting of HPV 16, 18, 31, 33, 35, 6, 51, and 59.
22. The immunogenic polypeptide of any one of embodiments 1 to 21, wherein said immunogenic polypeptide comprises three copies, more preferably two copies, most preferably one copy of each of said PV L2 N-terminal peptides.
23. The immunogenic polypeptide of any one of embodiments 1 to 22, wherein said thioredoxin is a human, bacterial, or an archaebacterial thioredoxin.
24. The immunogenic polypeptide of any one of embodiments 1 to 23, wherein said thioredoxin is a thioredoxin of a thermophilic archaebacterium, preferably of *Pyrococcus furiosus*, preferably having the sequence of SEQ ID NO:19.
25. The immunogenic polypeptide of any one of embodiments 1 to 24, wherein said T-cell epitope and/or said B-cell epitope is or are comprised in the display site of said thioredoxin.
26. The immunogenic polypeptide of any one of embodiments 1 to 25, wherein said immunogenic polypeptide further comprises an oligomerization domain.
27. The immunogenic polypeptide of embodiment 26, wherein said oligomerization domain is at least one of
(i) a hybrid polypeptide of two different chicken C4-binding proteins, preferably an IMX313Tpolypeptide;
(ii) an encapsulin polypeptide, preferably an encapsulin polypeptide from a thermophilic archaebacterium, more preferably a *Pyrococcus furiosus* encapsulin polypeptide;
(iii) a ferritin polypeptide, preferably a ferritin polypeptide from a thermophilic archaebacterium, more preferably a *Pyrococcus furiosus* ferritin polypeptide; and
(iv) an oligomerization domain of a C4-binding protein, preferably of a mammalian C4-binding protein, more preferably of a human or mouse C4-binding protein, most preferably of a mouse C4-binding protein.
28. The immunogenic polypeptide of embodiment 26 or 27, wherein said oligomerization domain comprises, preferably consists of, SEQ ID NO:29.
29. The immunogenic polypeptide of any one of embodiments 1 to 28, wherein said immunogenic polypeptide comprises a peptide comprising a multitude of PV L2 N-terminal peptides, wherein said peptide comprising a multitude of PV L2 N-terminal peptides has the amino acid sequence of SEQ ID NO:1 or a sequence at least 80% identical to SEQ ID NO:1.
30. The immunogenic polypeptide of any one of embodiments 1 to 29, wherein said immunogenic polypeptide comprises the amino acid sequence of SEQ ID NO:1 or a sequence at least 80% identical to said sequence and the amino acid sequence of SEQ ID NO:2, or a sequence at least 80% identical to said sequence.
31. The immunogenic polypeptide of any one of embodiments 1 to 30, wherein said immunogenic polypeptide comprises the amino acid sequence of SEQ ID NO:3 or a sequence at least 80% identical to said sequence.
32. The immunogenic polypeptide of any one of embodiments 1 to 31, wherein said immunogenic polypeptide comprises the amino acid sequence of SEQ ID NO: 4 or a sequence at least 80% identical to said sequence.
33. The immunogenic polypeptide of any one of embodiments 1 to 32, wherein said immunogenic polypeptide comprises
(i) the amino acid sequence of SEQ ID NO:5;
(ii) an amino acid sequence at least 70% identical to the amino acid sequence of SEQ ID NO:5;
(iii) a polypeptide sequence encoded by SEQ ID NO:34; and/or
(iv) a polypeptide encoded by a polynucleotide sequence at least 70% identical to the sequence of SEQ ID NO:34.
34. An immunogenic polypeptide according to any one of embodiments 1 to 33 for use in medicine.
35. An immunogenic polypeptide according to any one of embodiments 1 to 33 for use in treating and/or preventing inappropriate proliferation of cells and/or infection with an infectious agent, preferably HPV infection.
36. The immunogenic polypeptide for use of embodiment 35 for use in treating and preventing HPV infection.

37. A polynucleotide encoding the immunogenic polypeptide according to any one of embodiments 1 to 33, preferably comprising the sequence of SEQ ID NO:33 or a sequence at least 80% identical thereto, more preferably comprising the sequence of SEQ ID NO:34 or a sequence at least 80% identical thereto.
38. A vector comprising the polynucleotide according to embodiment 37.
39. A host cell comprising the immunogenic polypeptide according to any one of embodiments 1 to 33, the polynucleotide according to embodiment 37, and/or the vector according to embodiment 38.
40. A pharmaceutical composition comprising the immunogenic polypeptide according to any one of embodiments 1 to 33, the polynucleotide according to embodiment 37, and/or the vector according to embodiment 38.
41. A kit comprising the immunogenic polypeptide according to any one of embodiments 1 to 33, the polynucleotide according to embodiment 37, the host cell according to embodiment 39, and/or the vector according to embodiment 38, comprised in a housing.
42. The polypeptide according to any one of embodiments 1 to 33, the polynucleotide according to embodiment 37, the vector according to embodiment 38, the host cell according to embodiment 39, and/or the pharmaceutical composition according to embodiment 40 for use in medicine
43. The polypeptide according to any one of embodiments 1 to 33, the polynucleotide according to embodiment 37, the vector according to embodiment 38, the host cell according to embodiment 39, and/or the pharmaceutical composition according to embodiment 40 for use in treating and/or preventing inappropriate proliferation of cells and/or infection with an infectious agent, preferably HPV infection.
44. A method of treating and/or preventing inappropriate proliferation of cells and/or infection with an infectious agent, preferably HPV infection, comprising contacting a subject with the immunogenic polypeptide according to any one of embodiments 1 to 33, the polynucleotide according to embodiment 37, the vector according to embodiment 38, the host cell according to embodiment 39, and/or the pharmaceutical composition according to embodiment 40 and, thereby, treating and/or preventing HPV infection.
45. The method of embodiment 44, wherein said subject is suffering from at least one PV-related lesion.
46. The method of embodiment 44 or 45, wherein said subject is a subject at risk of becoming infected with a PV.
47. The method of any one of embodiments 44 to 46, wherein said subject is a human at an age of at most 16 years, preferably at most 15 years, more preferably at most 14 years, even more preferably at most 13 years, most preferably at most 12 years.
48. A composition comprising an anti-PV antibody and/or anti-PV T cells produced or producible by contacting a subject with the immunogenic polypeptide according to any one of embodiments 1 to 33, the polynucleotide according to embodiment 37, the vector according to embodiment 38, the host cell according to embodiment 39, and/or the pharmaceutical composition according to embodiment 40, preferably wherein said subject is non-human.

All references cited in this specification are herewith incorporated by reference with respect to their entire disclosure content and the disclosure content specifically mentioned in this specification.

FIGURE LEGENDS

FIG. 1: Schematic representation of a preferred embodiment of an immunogenic polypeptide according to the present invention.

Figure 2:
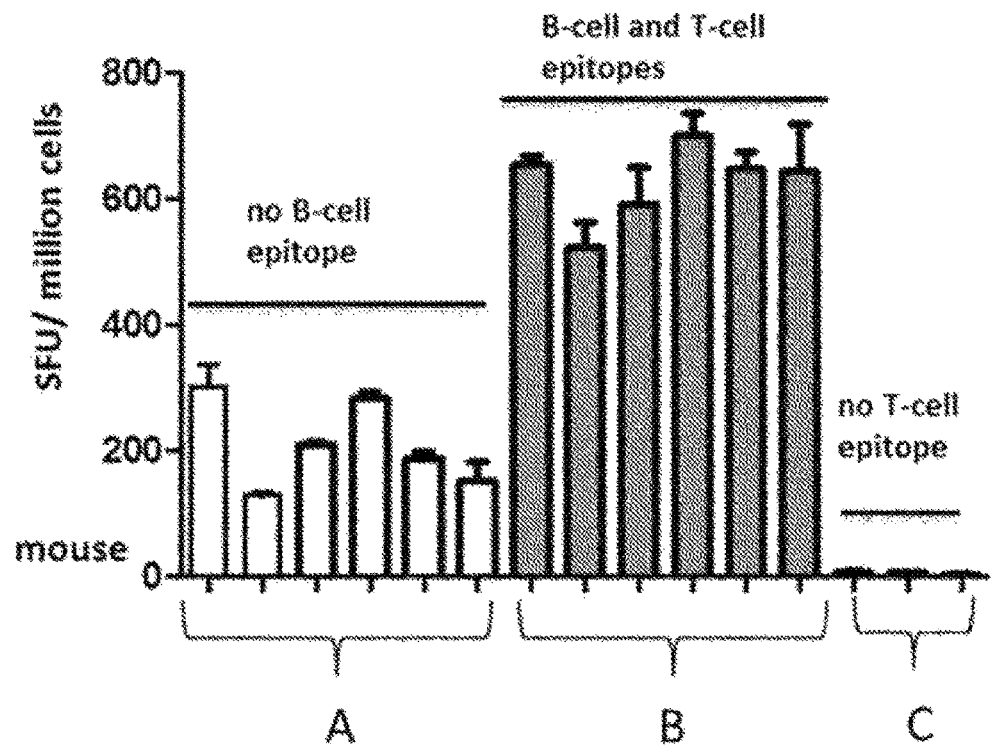

FIG. 2: Number of spot forming units/million cells in the T-cell activation assay of Example 1. A: mice immunized with PfTrx-(OVA257-264)3X-OVX313, B: mice immunized with PfTrx-L2(20-38)8mer-(OVA257-264)3X-OVX313, C: mice immunized with PfTrx-L2(20-38)8mer-OVX313.

Figure 3:
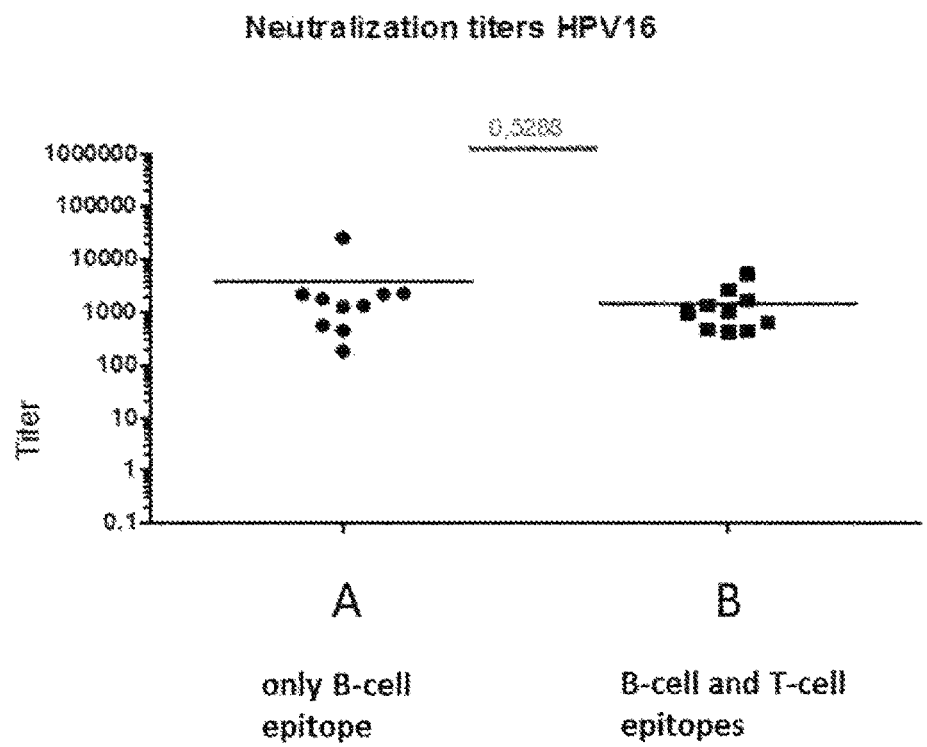

FIG. 3: Anti-HPV16 neutralization titers of mice immunized according to Example 2. Antigens were A: PfTrx-L2(20-38)8mer-OVX313; B: Pffrx-L2(20-38)8mer-(OVA257-264)3X-OVX313).

Figure 4:
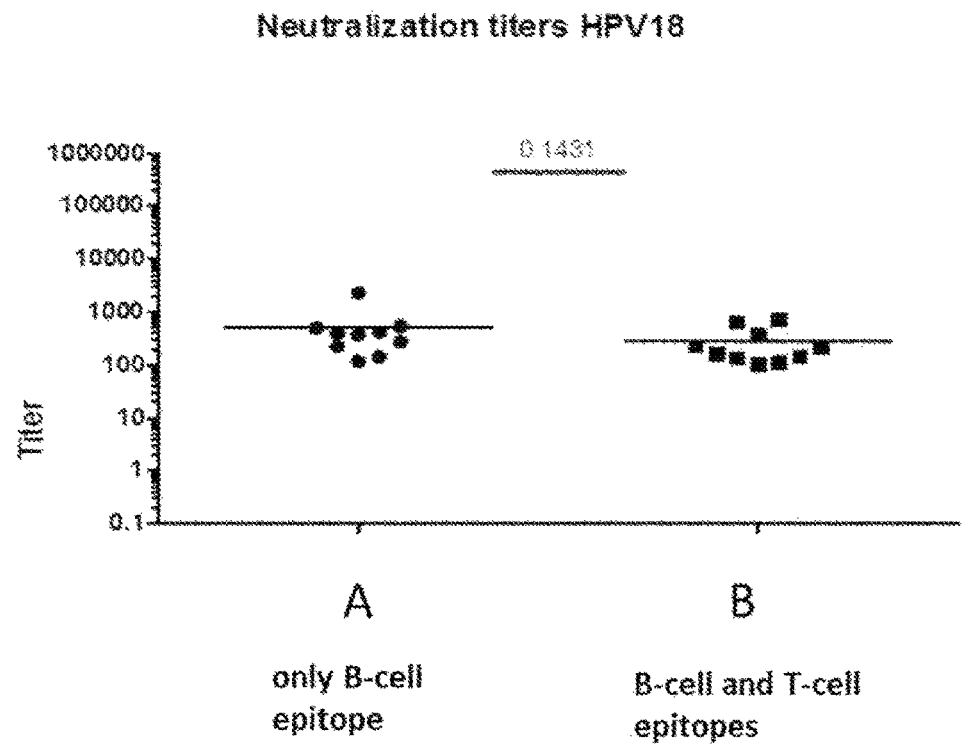

FIG. 4: Anti-HPV18 neutralization titers of mice immunized according to Example 3. Antigens were A: PfFrx-L2(20-38)8mer-OVX313; B: Pffrx-L2(20-38)8mer-(OVA257-264)3X-OVX313).

Figure 5:
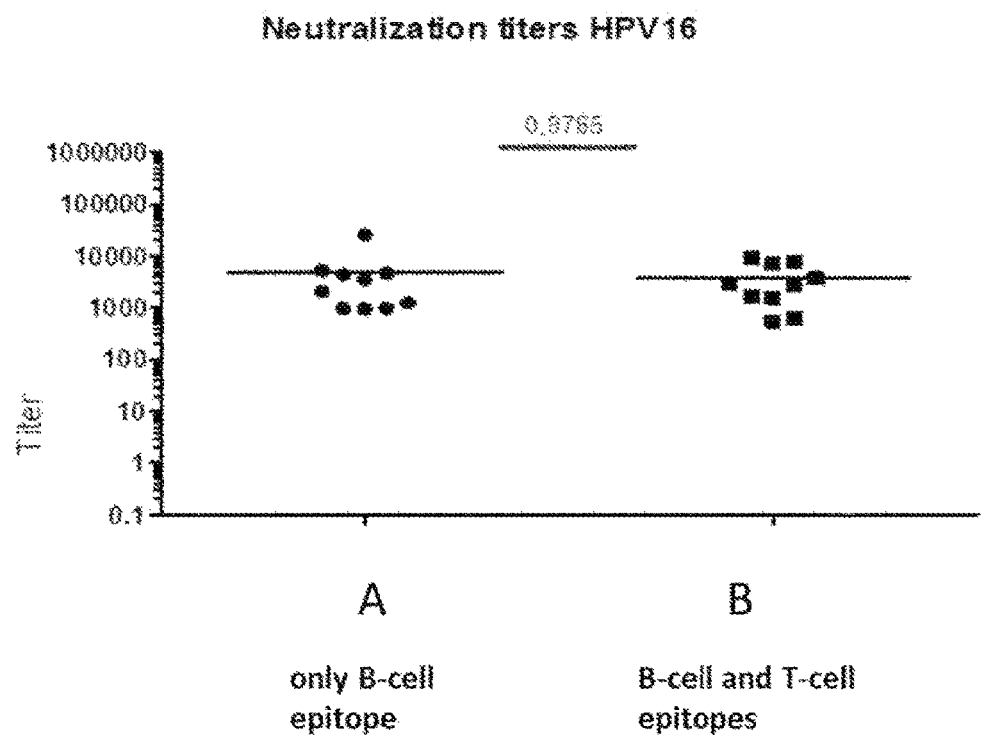

FIG. 5: Same as FIG. 3, but results from Example 4, i.e. group B was immunized with PfTrx-L2(20-38)8mer-(flankE7(49-57))3X-OVX313).

Figure 6:
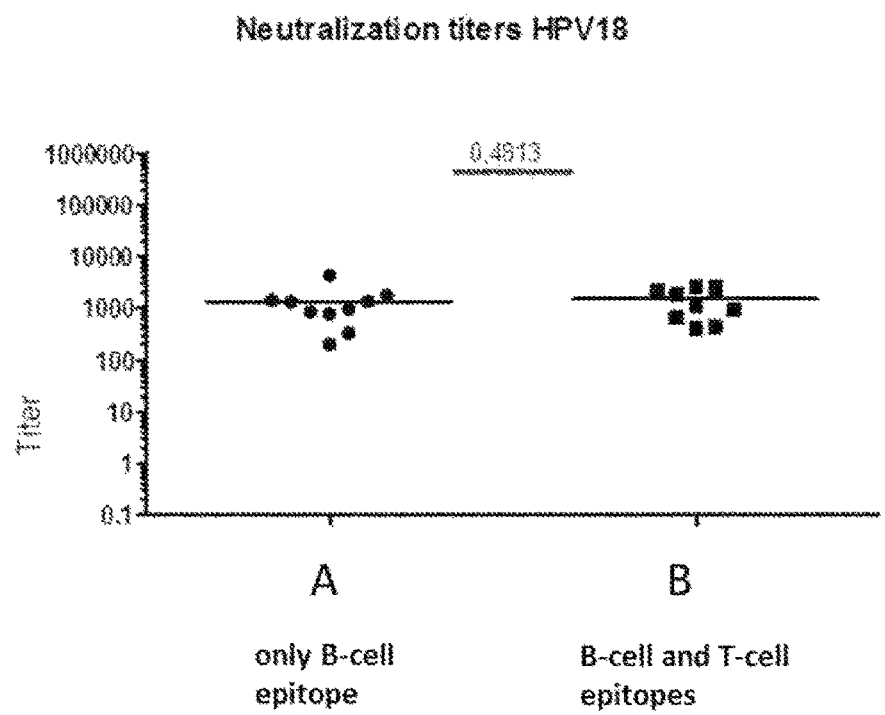

FIG. 6: Same as FIG. 4, but results from Example 4, i.e. group B was immunized with Pffrx-L2(20-38)8mer-(flankE7(49-57))3X-OVX313).

Figure 7:
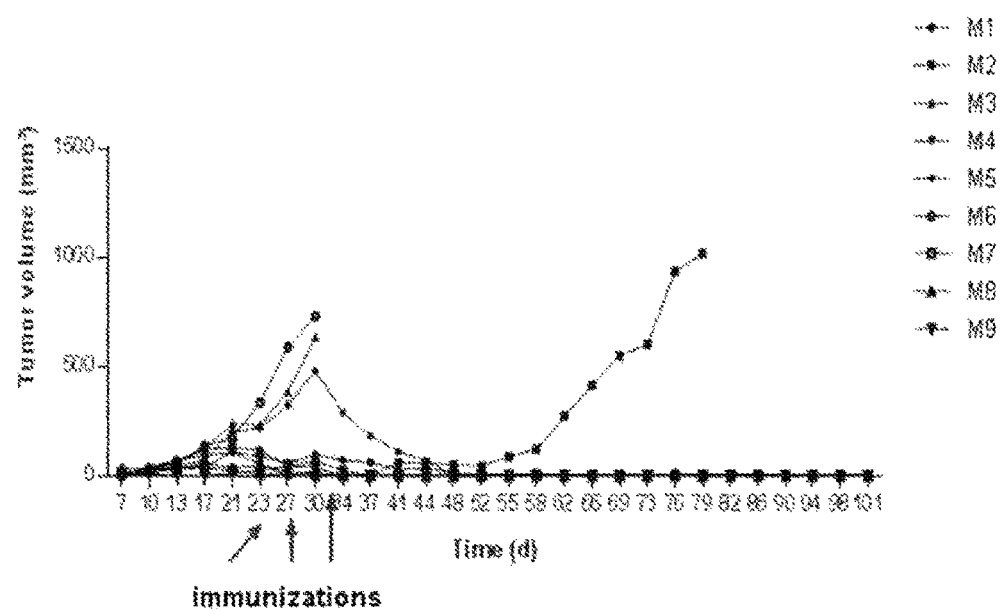
Figure 7:
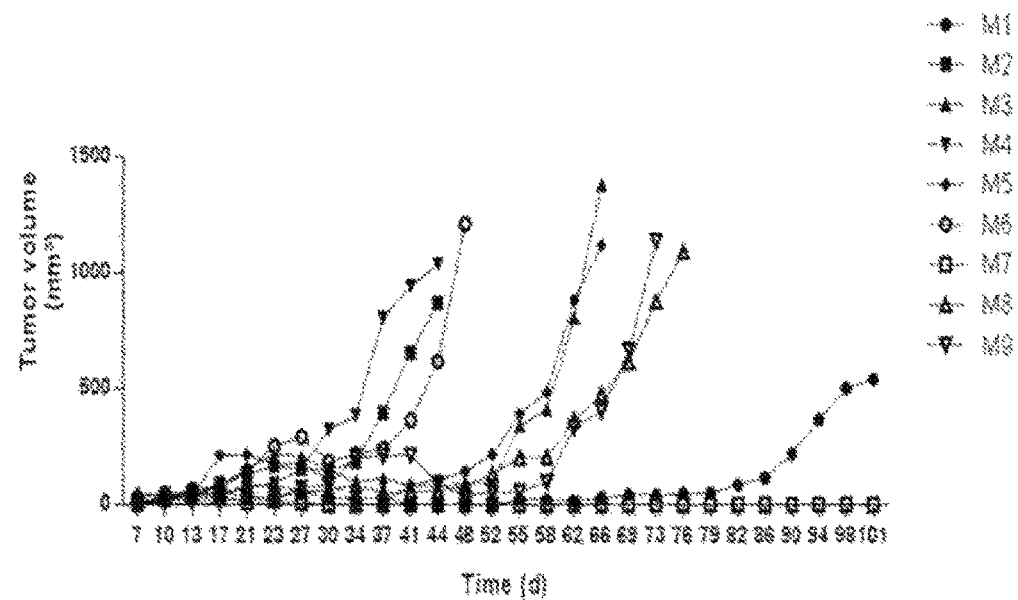

FIG. 7: Tumor growth over time in vaccinated (A) and non-vaccinated (B) mice of Example 6. M1 to M9 indicates numbers of mice.

Figure 8:
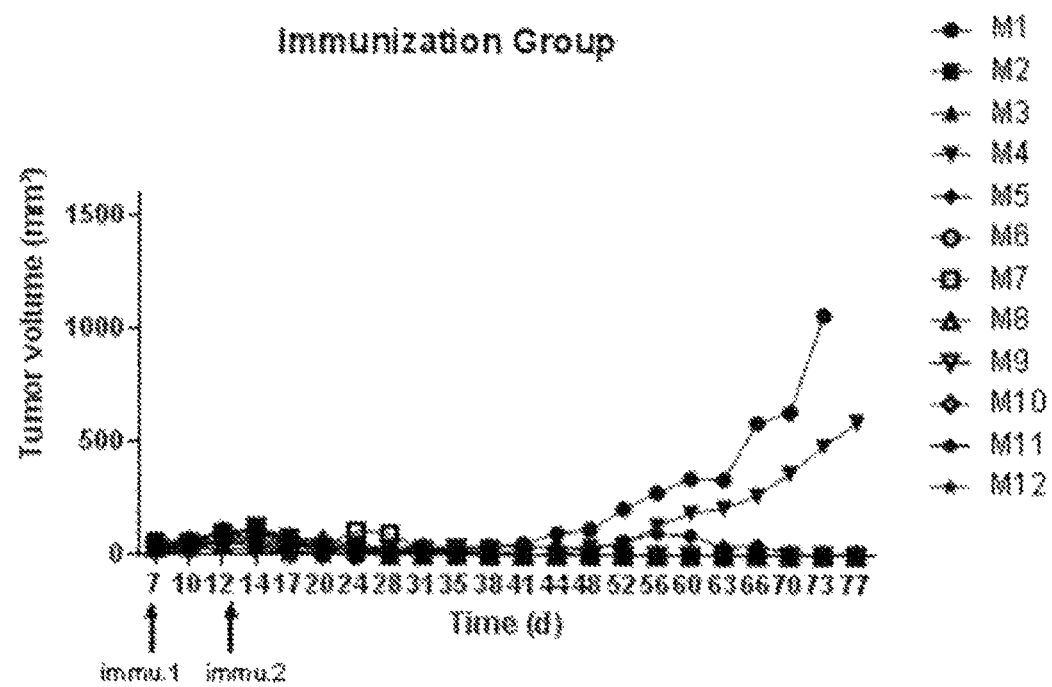
Figure 8:
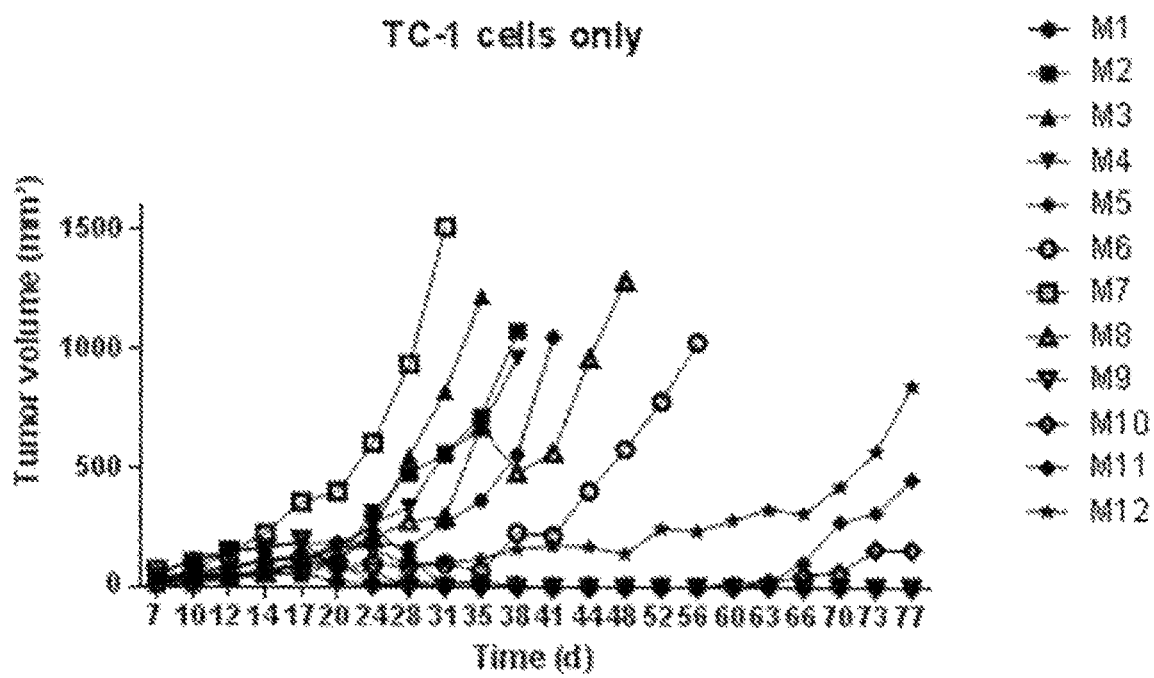

FIG. 8: Tumor growth over time in vaccinated (A) and non-vaccinated (B) mice of Example 7. M1 to M12 indicates numbers of mice.

The following Examples shall merely illustrate the invention. They shall not be construed, whatsoever, to limit the scope of the invention.

EXAMPLE 1

6 to 8 week-old C57BL/6N female mice (6 or 3 per group) were immunized with 20 μg PfTrx-(OVA257-264)3X-OVX313; PfTrx-L2(20-38)8mer-(OVA257-264)3X-OVX313; or PfTrx-L2(20-38)8mer-OVX313 (plus Addavax 50% (v/v) at the base of the tail subcutaneously. 7 days later, splenocytes were obtained, then IFN-gamma Elispot was performed with in vitro stimulation by OVA257-264 peptide. The OVA257-264 peptide is the T-cell epitope from ovalbumin corresponding to amino acids 257-264. OVX313 is the IMX313 oligomerization domain, Pffrx is the thioredoxin of *Pyrococcus furiosus*, L2(20-38)8mer is the peptide having the amino acid sequence of SEQ ID NO:1, all as described elsewhere herein. As shown in FIG. 2, the antigen containing both B-cell and T-cell epitopes stimulates an increased anti-OVA T cell response compared to the B-cell epitope only.

EXAMPLE 2

6 to 8 week-old BALB/c female mice (10 per group) were intramuscularly immunized 4 times with 2 weeks as immunization interval. The amount of 20 μg different antigens (PfTrx-L2(20-38)8mer-OVX313 or PfTrx-L2(20-38)8mer-(OVA257-264)3X-OVX313) was used with Addavax 50% (v/v) as immune-adjuvant. Sera were collected from mice one month after the last immunization and analyzed against HPV 16 pseudovirions using the L1-PBNA (pseudovirion-based neutralization assay). As shown in FIG. 3, an antigen containing both B-cell and T-cell epitopes produces comparable anti-HPV16 neutralizing antibody titers compared to the antigen with only B cell epitope.

EXAMPLE 3

6 to 8 week-old BALB/c female mice (10 per group) were intramuscularly immunized 4 times with 2 weeks as immunization interval. The amount of 20 µg of different antigens (Pffrx-L2(20-38)8mer-OVX313 or PfTrx-L2(20-38)8mer-(OVA257-264)3X-OVX313) was used with Addavax 50% (v/v). Sera collected from mice one month after the last immunization and analyzed against HPV 18 pseudovirions using the L1-PBNA (pseudovirion-based neutralization assay). As shown in FIG. 4, an antigen containing both B-cell and ovalbumin-T-cell epitopes produces comparable anti-HPV18 neutralizing antibody titers compared to the antigen with only B cell epitope.

EXAMPLE 4

6 to 8 week-old BALB/c female mice (10 per group) were intramuscularly immunized 4 times with 2 weeks as immunization interval. The amount of 20 µg different antigens (Pffrx-L2(20-38)8mer-OVX313 or Pffrx-L2(20-38)8mer-(flankE749-57)3X-OVX313) was used with Addavax 50% (v/v). Sera collected from mice one month after the last immunization and analyzed against HPV 16 pseudovirions using the L1-PBNA (pseudovirion-based neutralization assay). As shown in FIG. 5, an antigen containing both B-cell and E7-T-cell epitopes produces comparable anti-HPV16 neutralizing antibody titers compared to the antigen with only B cell epitope.

EXAMPLE 5

The 6 to 8 week-old BALB/c female mice (10 per group) were intramuscularly immunized 4 times with 2 weeks as immunization interval. The amount of 20 µg different antigens (A. PfTrx-L2(20-38)8mer-OVX313; B. PfTrx-L2(20-38)8mer-(flank E749-57)3X-OVX313) was used with Addavax 50% (v/v). Sera collected from mice one month after the last immunization and analyzed against HPV 18 pseudovirions using the L1-PBNA (pseudovirion-based neutralization assay). As shown in FIG. 6, an antigen containing both B-cell and E7-T-cell epitopes produces comparable anti-HPV18 neutralizing antibody titers compared to the antigen with only B cell epitope.

EXAMPLE 6

18 C57BL/6N mice were subcutaneously injected with $0.2 \times 10^6$ of TC-1 tumor cells (i.e. cells derived from lung epithelium of C57BL/6 mice, transformed with HPV E6, E7 and c-Ha ras) into the right flank. Half of the tumor mice (9 out of 18 mice) were immunized at day 23, 27 and 31 with 20 µg antigen PfTrx-L2(20-38)8mer-(flankE7(49-57))3X-OVX313 (plus Addavax 50% (v/v)) at the base of the tail subcutaneously. The other 9 tumor mice were not vaccinated. Tumor size was measured with a caliper every 3 or 4 days. Mice were sacrificed when the tumor volume was over 1 cm$^3$ or the tumor diameter was over 1.5 cm. As shown in FIG. 7, vaccinated mice (A) show strongly impeded tumor growth compared to the non-vaccinated controls (B).

EXAMPLE 7

24 C57BL/6N mice were subcutaneously injected with $0.2 \times 10^6$ of TC-1 tumor cells into the right flank. Half of the tumor mice (12 out of 24 mice) were immunized at day 7 and 12 with g antigen PfTrx-L2(20-38)8mer-(flankE7(49-57))3X-OVX313 (plus Addavax 50% (v/v)) at the base of the tail subcutaneously. The other 12 tumor mice not vaccinated. Tumor size was measured with a caliper every 3 or 4 days. Mice were sacrificed when the tumor volume was over 1 cm$^3$ or the tumor diameter was over 1.5 cm. As shown in FIG. 8, vaccinated mice (A) show strongly impeded tumor growth compared to the non-vaccinated controls (B), indicating that two times vaccination is sufficient to induce a strong anti-tumor response.

The invention claimed is:

1. An immunogenic polypeptide comprising (i) a B-cell epitope, (ii) a T-cell epitope, and (iii) a scaffold polypeptide, wherein said scaffold polypeptide is a thioredoxin polypeptide.

2. The immunogenic polypeptide of claim 1, wherein at least one of said B-cell epitope and said T-cell epitope is an epitope of an antigen of an infectious agent and/or of a tumor antigen.

3. The immunogenic polypeptide of claim 1, wherein both the B-cell epitope and the T-cell epitope are epitopes of papillomavirus (PV) polypeptides.

4. The immunogenic polypeptide of claim 1, wherein said B-cell epitope and said T-cell epitope are derived from non-identical polypeptides, more preferably are derived from non-homologous polypeptides.

5. The immunogenic polypeptide of claim 1, wherein said T-cell epitope is a peptide derived from an E6 or E7 polypeptide, preferably from an E7 polypeptide.

6. The immunogenic polypeptide of claim 1, wherein said B-cell epitope is a peptide corresponding to amino acids 20 to 38 of the L2 polypeptide of HPV16.

7. The immunogenic polypeptide of claim 1, wherein said immunogenic polypeptide comprises PV L2 N-terminal peptides from at least two, preferably at least four, more preferably at least six, most preferably all HPV genotypes selected from the list consisting of HPV 16, 18, 31, 33, 35, 6, 51, and 59.

8. The immunogenic polypeptide of claim 1, wherein said thioredoxin is a thioredoxin of a thermophilic archaebacterium.

9. The immunogenic polypeptide of claim 1, wherein said immunogenic polypeptide further comprises an oligomerization domain.

10. The immunogenic polypeptide of claim 1, wherein said immunogenic polypeptide comprises the amino acid sequence of SEQ ID NO:3 or a sequence at least 80% identical to said sequence.

11. The immunogenic polypeptide of claim 1, wherein said immunogenic polypeptide comprises the amino acid sequence of SEQ ID NO.4.

12. A method of treating and/or preventing inappropriate proliferation of cells and/or infection with an infectious agent, comprising contacting a subject with the immunogenic polypeptide according to claim 1 and, thereby, treating and/or preventing HPV infection.

13. The method of claim 12, wherein said subject is suffering from at least one PV-related lesion.

14. The method of claim 12, wherein the infection with the infectious agent is an HPV infection.

* * * * *

SEQUENCE LISTING

```
<160> NUMBER OF SEQ ID NOS: 34

<210> SEQ ID NO 1
<211> LENGTH: 173
<212> TYPE: PRT
<213> ORGANISM: Artificial
<220> FEATURE:
<223> OTHER INFORMATION: L2(20-38)8mer

<400> SEQUENCE: 1

Lys Thr Cys Lys Gln Ala Gly Thr Cys Pro Pro Asp Ile Ile Pro Lys
1               5                   10                  15

Val Glu Gly Gly Gly Pro Lys Thr Cys Lys Gln Ser Gly Thr Cys Pro
            20                  25                  30

Pro Asp Val Val Pro Lys Val Glu Gly Gly Gly Pro Gln Thr Cys Lys
        35                  40                  45

Ala Ala Gly Thr Cys Pro Ser Asp Val Ile Pro Lys Ile Glu His Gly
    50                  55                  60

Gly Pro Gln Thr Cys Lys Ala Thr Gly Thr Cys Pro Pro Asp Val Ile
65                  70                  75                  80
```

```
Pro Lys Val Glu Gly Gly Pro Arg Thr Cys Lys Ala Ala Gly Thr
            85                  90                  95

Cys Pro Pro Asp Val Ile Pro Lys Val Glu Gly Gly Pro Gln Thr
            100                 105                 110

Cys Lys Leu Thr Gly Thr Cys Pro Pro Asp Val Ile Pro Lys Val Glu
            115                 120                 125

His Gly Gly Pro Ser Thr Cys Lys Ala Ala Gly Thr Cys Pro Pro Asp
            130                 135                 140

Val Val Asn Lys Val Glu Gly Gly Pro Lys Thr Cys Lys Gln Ala
145                 150                 155                 160

Gly Thr Cys Pro Ser Asp Val Ile Asn Lys Val Glu Gly
            165                 170

<210> SEQ ID NO 2
<211> LENGTH: 63
<212> TYPE: PRT
<213> ORGANISM: Artificial
<220> FEATURE:
<223> OTHER INFORMATION: E7(49-57)

<400> SEQUENCE: 2

Gln Ala Glu Pro Asp Arg Ala His Tyr Asn Ile Val Thr Phe Cys Cys
1               5                   10                  15

Lys Cys Asp Gly Gly Pro Gln Ala Glu Pro Asp Arg Ala His Tyr Asn
            20                  25                  30

Ile Val Thr Phe Cys Cys Lys Cys Asp Gly Gly Pro Gln Ala Glu Pro
            35                  40                  45

Asp Arg Ala His Tyr Asn Ile Val Thr Phe Cys Cys Lys Cys Asp
            50                  55                  60

<210> SEQ ID NO 3
<211> LENGTH: 239
<212> TYPE: PRT
<213> ORGANISM: Artificial
<220> FEATURE:
<223> OTHER INFORMATION: L2-8mer/FlankE7-3mer

<400> SEQUENCE: 3

Lys Thr Cys Lys Gln Ala Gly Thr Cys Pro Pro Asp Ile Ile Pro Lys
1               5                   10                  15

Val Glu Gly Gly Gly Pro Lys Thr Cys Lys Gln Ser Gly Thr Cys Pro
            20                  25                  30

Pro Asp Val Val Pro Lys Val Glu Gly Gly Pro Gln Thr Cys Lys
            35                  40                  45

Ala Ala Gly Thr Cys Pro Ser Asp Val Ile Pro Lys Ile Glu His Gly
50                  55                  60

Gly Pro Gln Thr Cys Lys Ala Thr Gly Thr Cys Pro Pro Asp Val Ile
65                  70                  75                  80

Pro Lys Val Glu Gly Gly Pro Arg Thr Cys Lys Ala Ala Gly Thr
            85                  90                  95

Cys Pro Pro Asp Val Ile Pro Lys Val Glu Gly Gly Pro Gln Thr
            100                 105                 110

Cys Lys Leu Thr Gly Thr Cys Pro Pro Asp Val Ile Pro Lys Val Glu
            115                 120                 125

His Gly Gly Pro Ser Thr Cys Lys Ala Ala Gly Thr Cys Pro Pro Asp
            130                 135                 140

Val Val Asn Lys Val Glu Gly Gly Gly Pro Lys Thr Cys Lys Gln Ala
```

```
145                 150                 155                 160
Gly Thr Cys Pro Ser Asp Val Ile Asn Lys Val Glu Gly Gly Pro
                165                 170                 175
Gln Ala Glu Pro Asp Arg Ala His Tyr Asn Ile Val Thr Phe Cys Cys
                180                 185                 190
Lys Cys Asp Gly Gly Pro Gln Ala Glu Pro Asp Arg Ala His Tyr Asn
                195                 200                 205
Ile Val Thr Phe Cys Cys Lys Cys Asp Gly Gly Pro Gln Ala Glu Pro
        210                 215                 220
Asp Arg Ala His Tyr Asn Ile Val Thr Phe Cys Cys Lys Cys Asp
225                 230                 235

<210> SEQ ID NO 4
<211> LENGTH: 339
<212> TYPE: PRT
<213> ORGANISM: Artificial
<220> FEATURE:
<223> OTHER INFORMATION: Trx/L2-8mer/FlankE7-3mer

<400> SEQUENCE: 4

Glu Tyr Asp Gly Glu Ile Asp Phe Thr Lys Gly Arg Val Val Leu Trp
1               5                   10                  15
Phe Ser Ile Pro Gly Cys Gly Pro Lys Thr Cys Lys Gln Ala Gly Thr
                20                  25                  30
Cys Pro Pro Asp Ile Ile Pro Lys Val Glu Gly Gly Pro Lys Thr
            35                  40                  45
Cys Lys Gln Ser Gly Thr Cys Pro Pro Asp Val Val Pro Lys Val Glu
        50                  55                  60
Gly Gly Pro Gln Thr Cys Lys Ala Ala Gly Thr Cys Pro Ser Asp
65              70                  75                  80
Val Ile Pro Lys Ile Glu His Gly Gly Pro Gln Thr Cys Lys Ala Thr
                85                  90                  95
Gly Thr Cys Pro Pro Asp Val Ile Pro Lys Val Glu Gly Gly Pro
            100                 105                 110
Arg Thr Cys Lys Ala Ala Gly Thr Cys Pro Pro Asp Val Ile Pro Lys
            115                 120                 125
Val Glu Gly Gly Pro Gln Thr Cys Lys Leu Thr Gly Thr Cys Pro
        130                 135                 140
Pro Asp Val Ile Pro Lys Val Glu His Gly Gly Pro Ser Thr Cys Lys
145                 150                 155                 160
Ala Ala Gly Thr Cys Pro Pro Asp Val Val Asn Lys Val Glu Gly Gly
                165                 170                 175
Gly Pro Lys Thr Cys Lys Gln Ala Gly Thr Cys Pro Ser Asp Val Ile
                180                 185                 190
Asn Lys Val Glu Gly Gly Gly Pro Gln Ala Glu Pro Asp Arg Ala His
            195                 200                 205
Tyr Asn Ile Val Thr Phe Cys Cys Lys Cys Asp Gly Gly Pro Gln Ala
        210                 215                 220
Glu Pro Asp Arg Ala His Tyr Asn Ile Val Thr Phe Cys Cys Lys Cys
225                 230                 235                 240
Asp Gly Gly Pro Gln Ala Glu Pro Asp Arg Ala His Tyr Asn Ile Val
                245                 250                 255
Thr Phe Cys Cys Lys Cys Asp Gly Gly Pro Cys Arg Leu Val Glu Arg
            260                 265                 270
Phe Met Thr Glu Leu Ser Glu Tyr Phe Glu Asp Ile Gln Ile Val His
```

```
                      275                 280                 285

Ile Asn Ala Gly Lys Trp Lys Asn Ile Val Asp Lys Phe Asn Ile Leu
    290                 295                 300

Asn Val Pro Thr Leu Val Tyr Leu Lys Asp Gly Arg Glu Val Gly Arg
305                 310                 315                 320

Gln Asn Leu Ile Arg Ser Lys Glu Glu Ile Leu Lys Lys Leu Lys Glu
                325                 330                 335

Leu Gln Glu

<210> SEQ ID NO 5
<211> LENGTH: 396
<212> TYPE: PRT
<213> ORGANISM: Artificial
<220> FEATURE:
<223> OTHER INFORMATION: Trx/L2-8mer/FlankE7-3mer/IMX313

<400> SEQUENCE: 5

Glu Tyr Asp Gly Glu Ile Asp Phe Thr Lys Gly Arg Val Val Leu Trp
1               5                   10                  15

Phe Ser Ile Pro Gly Cys Gly Pro Lys Thr Cys Lys Gln Ala Gly Thr
                20                  25                  30

Cys Pro Pro Asp Ile Ile Pro Lys Val Glu Gly Gly Pro Lys Thr
            35                  40                  45

Cys Lys Gln Ser Gly Thr Cys Pro Pro Asp Val Val Pro Lys Val Glu
50                  55                  60

Gly Gly Gly Pro Gln Thr Cys Lys Ala Ala Gly Thr Cys Pro Ser Asp
65                  70                  75                  80

Val Ile Pro Lys Ile Glu His Gly Gly Pro Gln Thr Cys Lys Ala Thr
                85                  90                  95

Gly Thr Cys Pro Pro Asp Val Ile Pro Lys Val Glu Gly Gly Pro
            100                 105                 110

Arg Thr Cys Lys Ala Ala Gly Thr Cys Pro Pro Asp Val Ile Pro Lys
                115                 120                 125

Val Glu Gly Gly Gly Pro Gln Thr Cys Lys Leu Thr Gly Thr Cys Pro
            130                 135                 140

Pro Asp Val Ile Pro Lys Val Glu His Gly Gly Pro Ser Thr Cys Lys
145                 150                 155                 160

Ala Ala Gly Thr Cys Pro Pro Asp Val Val Asn Lys Val Glu Gly Gly
                165                 170                 175

Gly Pro Lys Thr Cys Lys Gln Ala Gly Thr Cys Pro Ser Asp Val Ile
            180                 185                 190

Asn Lys Val Glu Gly Gly Gly Pro Gln Ala Glu Pro Asp Arg Ala His
            195                 200                 205

Tyr Asn Ile Val Thr Phe Cys Cys Lys Cys Asp Gly Pro Gln Ala
            210                 215                 220

Glu Pro Asp Arg Ala His Tyr Asn Ile Val Thr Phe Cys Cys Lys Cys
225                 230                 235                 240

Asp Gly Gly Pro Gln Ala Glu Pro Asp Arg Ala His Tyr Asn Ile Val
            245                 250                 255

Thr Phe Cys Cys Lys Cys Asp Gly Gly Pro Cys Arg Leu Val Glu Arg
            260                 265                 270

Phe Met Thr Glu Leu Ser Glu Tyr Phe Glu Asp Ile Gln Ile Val His
            275                 280                 285

Ile Asn Ala Gly Lys Trp Lys Asn Ile Val Asp Lys Phe Asn Ile Leu
    290                 295                 300
```

Asn Val Pro Thr Leu Val Tyr Leu Lys Asp Gly Arg Glu Val Gly Arg
305                 310                 315                 320

Gln Asn Leu Ile Arg Ser Lys Glu Glu Ile Leu Lys Lys Leu Lys Glu
            325                 330                 335

Leu Gln Glu Gly Ser Lys Lys Gly Asp Ala Asp Val Cys Gly Glu
            340                 345                 350

Val Ala Tyr Ile Gln Ser Val Val Ser Asp Cys His Val Pro Thr Ala
            355                 360                 365

Glu Leu Arg Thr Leu Leu Glu Ile Arg Lys Leu Phe Leu Glu Ile Gln
        370                 375                 380

Lys Leu Lys Val Glu Gly Arg Arg Arg Arg Ser
385                 390                 395

<210> SEQ ID NO 6
<211> LENGTH: 36
<212> TYPE: PRT
<213> ORGANISM: Human papillomavirus type 16

<400> SEQUENCE: 6

Ala Thr Gln Leu Tyr Lys Thr Cys Lys Gln Ala Gly Thr Cys Pro Pro
1               5                   10                  15

Asp Ile Ile Pro Lys Val Glu Gly Lys Thr Ile Ala Glu Gln Ile Leu
            20                  25                  30

Gln Tyr Gly Ser
        35

<210> SEQ ID NO 7
<211> LENGTH: 25
<212> TYPE: PRT
<213> ORGANISM: Human papillomavirus type 16

<400> SEQUENCE: 7

Gly Thr Gly Gly Arg Thr Gly Tyr Ile Pro Leu Gly Thr Arg Pro Pro
1               5                   10                  15

Thr Ala Thr Asp Thr Leu Ala Pro Val
            20                  25

<210> SEQ ID NO 8
<211> LENGTH: 19
<212> TYPE: PRT
<213> ORGANISM: Human papillomavirus type 16

<400> SEQUENCE: 8

Lys Thr Cys Lys Gln Ala Gly Thr Cys Pro Pro Asp Ile Ile Pro Lys
1               5                   10                  15

Val Glu Gly

<210> SEQ ID NO 9
<211> LENGTH: 9
<212> TYPE: PRT
<213> ORGANISM: Human papillomavirus type 16

<400> SEQUENCE: 9

Arg Ala His Tyr Asn Ile Val Thr Phe
1               5

<210> SEQ ID NO 10
<211> LENGTH: 5
<212> TYPE: PRT
<213> ORGANISM: Artificial

```
<220> FEATURE:
<223> OTHER INFORMATION: N-flank E7

<400> SEQUENCE: 10

Gln Ala Glu Pro Asp
1               5

<210> SEQ ID NO 11
<211> LENGTH: 5
<212> TYPE: PRT
<213> ORGANISM: Artificial
<220> FEATURE:
<223> OTHER INFORMATION: C-flank E7

<400> SEQUENCE: 11

Cys Cys Lys Cys Asp
1               5

<210> SEQ ID NO 12
<211> LENGTH: 19
<212> TYPE: PRT
<213> ORGANISM: Artificial
<220> FEATURE:
<223> OTHER INFORMATION: flank-E7

<400> SEQUENCE: 12

Gln Ala Glu Pro Asp Arg Ala His Tyr Asn Ile Val Thr Phe Cys Cys
1               5                   10                  15

Lys Cys Asp

<210> SEQ ID NO 13
<211> LENGTH: 105
<212> TYPE: PRT
<213> ORGANISM: Homo sapiens

<400> SEQUENCE: 13

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
                20                  25                  30

Gly Pro Cys Lys Met Ile Lys Pro Phe Phe His Ser Leu Ser Glu Lys
                35                  40                  45

Tyr Ser Asn Val Ile Phe Leu Glu Val Asp Val Asp Asp Cys Gln Asp
            50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
                100                 105

<210> SEQ ID NO 14
<211> LENGTH: 318
<212> TYPE: DNA
<213> ORGANISM: Artificial
<220> FEATURE:
<223> OTHER INFORMATION: Hs-Trx encoding

<400> SEQUENCE: 14
atggtgaagc agatcgagag caagactgct tttcaggaag ccttggacgc tgcaggtgat    60
aaacttgtag tagttgactt ctcagccacg tggtgtgggc cttgcaaaat gatcaagcct   120
```

```
ttctttcatt ccctctctga aaagtattcc aacgtgatat tccttgaagt agatgtggat      180
gactgtcagg atgttgcttc agagtgtgaa gtcaaatgca tgccaacatt ccagttttt       240 aagaagggac aaaaggtggg tgaattttct ggagccaata ggaaaagct tgaagccacc       300 attaatgaat tagtctaa                                                    318
```

<210> SEQ ID NO 15
<211> LENGTH: 105
<212> TYPE: PRT
<213> ORGANISM: Mus musculus

<400> SEQUENCE: 15

```
Met Val Lys Leu Ile Glu Ser Lys Glu Ala Phe Gln Glu Ala Leu Ala
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Cys Asp Lys
        35                  40                  45

Tyr Ser Asn Val Val Phe Leu Glu Val Asp Val Asp Asp Cys Gln Asp
    50                  55                  60

Val Ala Ala Asp Cys Glu Val Lys Cys Met Pro Thr Phe Gln Phe Tyr
65                  70                  75                  80

Lys Lys Gly Gln Lys Val Gly Glu Phe Ser Gly Ala Asn Lys Glu Lys
                85                  90                  95

Leu Glu Ala Ser Ile Thr Glu Tyr Ala
            100                 105
```

<210> SEQ ID NO 16
<211> LENGTH: 318
<212> TYPE: DNA
<213> ORGANISM: Artificial
<220> FEATURE:
<223> OTHER INFORMATION: Mm-Trx encoding

<400> SEQUENCE: 16

```
atggtgaagc tgatcgagag caaggaagct tttcaggagg ccctggccgc cgcgggagac      60
aagcttgtcg tggtggactt ctctgctacg tggtgcggtc cgtgcaaaat gatcaagccc     120
ttcttccatt ccctctgtga caagtattcc aatgtggtgt tccttgaagt ggatgtggat     180
gactgccagg atgttgctgc agactgtgaa gtcaaatgca tgccgacctt ccagttttat     240
aaaaagggtc aaaaggtggg ggagttctcc ggtgctaaca ggaaaagct tgaagcctct      300 attactgaat atgcctaa                                                   318
```

<210> SEQ ID NO 17
<211> LENGTH: 109
<212> TYPE: PRT
<213> ORGANISM: Escherichia coli

<400> SEQUENCE: 17

```
Met Gly Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60
```

| | | | | | | | | | | |
|---|---|---|---|---|---|---|---|---|---|---|
| Pro | Gly | Thr | Ala | Pro | Lys | Tyr | Gly | Ile | Arg | Gly | Ile | Pro | Thr | Leu | Leu |
| 65 | | | | 70 | | | | 75 | | | | 80 |

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

```
<210> SEQ ID NO 18
<211> LENGTH: 330
<212> TYPE: DNA
<213> ORGANISM: Artificial
<220> FEATURE:
<223> OTHER INFORMATION: Ec-Trx encoding

<400> SEQUENCE: 18
atgggcgata aaattattca cctgactgac gacagttttg acacggatgt actcaaagcg      60 gacgggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300
aaagagttcc tcgacgctaa cctggcgtga                                     330

<210> SEQ ID NO 19
<211> LENGTH: 100
<212> TYPE: PRT
<213> ORGANISM: Pyrococcus furiosus

<400> SEQUENCE: 19
```

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Cys Arg Leu Val Glu
                20                  25                  30

Arg Phe Met Thr Glu Leu Ser Glu Tyr Phe Glu Asp Ile Gln Ile Val
            35                  40                  45

His Ile Asn Ala Gly Lys Trp Lys Asn Ile Val Asp Lys Phe Asn Ile
        50                  55                  60

Leu Asn Val Pro Thr Leu Val Tyr Leu Lys Asp Gly Arg Glu Val Gly
65                  70                  75                  80

Arg Gln Asn Leu Ile Arg Ser Lys Glu Glu Ile Leu Lys Lys Leu Lys
                85                  90                  95

Glu Leu Gln Glu
            100

```
<210> SEQ ID NO 20
<211> LENGTH: 303
<212> TYPE: DNA
<213> ORGANISM: Artificial
<220> FEATURE:
<223> OTHER INFORMATION: Pf-Trx encoding

<400> SEQUENCE: 20
atgattatcg agtatgacgg cgaaatcgac ttcaccaaag gtcgtgttgt actgtggttt      60
agcattccgg gatgcggtcc gtgtcgtctg gttgaacgct tcatgaccga actgagcgag     120
tattttgagg atatccaaat tgtccatatc aatgccggca atggaaaaaa catcgtagac     180
aaattcaata ttctgaacgt gccgaccctg gtatatctga agatggccg tgaggttgga    240 cgccaaaacc tgattcgttc taagaagag attctgaaaa aactgaaaga gctgcaggag     300
```

```
                                                                        taa       303

<210> SEQ ID NO 21
<211> LENGTH: 138
<212> TYPE: PRT
<213> ORGANISM: Methanosarcina thermophila

<400> SEQUENCE: 21

Met Asp Glu Leu Asp Glu Ile Arg Arg Lys Lys Leu Glu Glu Leu Lys
1               5                   10                  15

Arg Glu Leu Ala Ala Arg Ser Gln Gly Thr Pro Thr Ile Glu Tyr Pro
            20                  25                  30

Asp Arg Pro Val Leu Val Thr Asp Ser Ser Ile Asp Ala Gly Ile Arg
        35                  40                  45

Gln Tyr Pro Val Phe Val Val Asp Cys Trp Ala Glu Trp Cys Gly Pro
    50                  55                  60

Cys Arg Ala Ile Ala Pro Val Ile Asp Glu Met Ala Arg Glu Leu Lys
65                  70                  75                  80

Gly Arg Val Val Phe Gly Lys Leu Asn Val Asp Gln Asn Pro Leu Thr
                85                  90                  95

Ser Arg Lys Tyr Gly Ile Thr Ala Ile Pro Thr Leu Leu Val Phe Arg
            100                 105                 110

Asn Gly Arg Leu Val Asp Arg Leu Val Gly Ala Tyr Pro Lys Gln Ile
        115                 120                 125

Leu Met Ser Arg Val Arg Lys Tyr Leu Asp
    130                 135

<210> SEQ ID NO 22
<211> LENGTH: 417
<212> TYPE: DNA
<213> ORGANISM: Artificial
<220> FEATURE:
<223> OTHER INFORMATION: Mt-Trx encoding

<400> SEQUENCE: 22
atggacgagc tggacgaaat ccgccgtaaa aaactggaag aactgaaacg tgaactggct        60
gcccgtagtc aaggaacacc gacgatcgag tatcctgacc gccctgtact ggttactgat       120
tctagcattg atgccgggat ccgccaatat cctgtctttg tggtggactg ttgggctgaa       180
tggtgcggtc cgtgtcgtgc tattgctccg gtgatcgatg aaatggcccg tgagctgaaa       240
ggacgtgtgg tattcgggaa actgaacgtg gaccaaaatc cgctgacgag tcgtaaatat       300
ggcattaccg ccatccctac actgctggtt ttccgtaacg gtcgtctggt tgatcgcctg       360
gttggtgctt atccgaaaca aattctgatg tctcgtgtcc gtaaatatct ggactag         417

<210> SEQ ID NO 23
<211> LENGTH: 3
<212> TYPE: PRT
<213> ORGANISM: Artificial
<220> FEATURE:
<223> OTHER INFORMATION: linker GGP

<400> SEQUENCE: 23

Gly Gly Pro
1

<210> SEQ ID NO 24
<211> LENGTH: 2
<212> TYPE: PRT
```

-continued

```
<213> ORGANISM: Artificial
<220> FEATURE:
<223> OTHER INFORMATION: linker GP

<400> SEQUENCE: 24

Gly Pro
1

<210> SEQ ID NO 25
<211> LENGTH: 2
<212> TYPE: PRT
<213> ORGANISM: Artificial
<220> FEATURE:
<223> OTHER INFORMATION: linker GS

<400> SEQUENCE: 25

Gly Ser
1

<210> SEQ ID NO 26
<211> LENGTH: 4
<212> TYPE: PRT
<213> ORGANISM: Artificial
<220> FEATURE:
<223> OTHER INFORMATION: linker GPGP

<400> SEQUENCE: 26

Gly Pro Gly Pro
1

<210> SEQ ID NO 27
<211> LENGTH: 5
<212> TYPE: PRT
<213> ORGANISM: Artificial
<220> FEATURE:
<223> OTHER INFORMATION: linker GPGPG

<400> SEQUENCE: 27

Gly Pro Gly Pro Gly
1               5

<210> SEQ ID NO 28
<211> LENGTH: 4
<212> TYPE: PRT
<213> ORGANISM: Artificial
<220> FEATURE:
<223> OTHER INFORMATION: linker SGSG

<400> SEQUENCE: 28

Ser Gly Ser Gly
1

<210> SEQ ID NO 29
<211> LENGTH: 55
<212> TYPE: PRT
<213> ORGANISM: Artificial
<220> FEATURE:
<223> OTHER INFORMATION: IMX313T-oligomerization domain

<400> SEQUENCE: 29

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
                20                  25                  30

Leu Glu Ile Arg Lys Leu Phe Leu Glu Ile Gln Lys Leu Lys Val Glu
            35                  40                  45
```

Gly Arg Arg Arg Arg Ser
    50                        55

<210> SEQ ID NO 30
<211> LENGTH: 519
<212> TYPE: DNA
<213> ORGANISM: Artificial
<220> FEATURE:
<223> OTHER INFORMATION: L2(20-38)8mer encoding

<400> SEQUENCE: 30

```
aagacctgca agcaagcggg tacctgcccg ccggacatca ttccgaaagt ggaaggtggc   60
ggtccgaaaa cctgcaagca agcggtacc tgcccgccgg atgttgttcc gaaagtggag   120
ggcggtggcc cgcaaacctg caaggcggcg ggtacctgcc cgagcgacgt tatcccgaag   180
attgaacatg gtggcccgca gacctgcaag gcgaccggca cctgcccgcc ggacgtgatc   240
ccgaaggttg agggtggcgg tccgcgtacc tgcaaagcgg cgggcacctg cccgccggat   300
gtgattccga aggttgaagg cggtggccct caaacctgca aactgactgg cacttgcccg   360
ccggacgtta ttccgaaggt tgagcatggt ggcccgagca cctgcaaagc tgctggaact   420
tgcccgccgg atgtggttaa caaggttgaa ggtggcggtc ctaaaacctg caagcaagcg   480
ggcacctgcc cgagcgacgt gatcaacaaa gttgaaggc                          519
```

<210> SEQ ID NO 31
<211> LENGTH: 189
<212> TYPE: DNA
<213> ORGANISM: Artificial
<220> FEATURE:
<223> OTHER INFORMATION: Flank-E7(49-57)3x encoding

<400> SEQUENCE: 31

```
caggcggagc cggatcgtgc gcactacaac attgtgacct tctgctgcaa atgcgatggt   60
ggcccgcaag cggaaccgga tcgtgcgcac tataacattg ttacctttg ctgcaagtgc   120
gatggtggcc cgcaggcgga accggaccgc gcgcactaca acatcgtgac cttttgttgt   180
aaatgtgat                                                           189
```

<210> SEQ ID NO 32
<211> LENGTH: 717
<212> TYPE: DNA
<213> ORGANISM: Artificial
<220> FEATURE:
<223> OTHER INFORMATION: L2-8mer/FlankE7-3mer encoding

<400> SEQUENCE: 32

```
aagacctgca agcaagcggg tacctgcccg ccggacatca ttccgaaagt ggaaggtggc   60
ggtccgaaaa cctgcaagca agcggtacc tgcccgccgg atgttgttcc gaaagtggag   120
ggcggtggcc cgcaaacctg caaggcggcg ggtacctgcc cgagcgacgt tatcccgaag   180
attgaacatg gtggcccgca gacctgcaag gcgaccggca cctgcccgcc ggacgtgatc   240
ccgaaggttg agggtggcgg tccgcgtacc tgcaaagcgg cgggcacctg cccgccggat   300
gtgattccga aggttgaagg cggtggccct caaacctgca aactgactgg cacttgcccg   360
ccggacgtta ttccgaaggt tgagcatggt ggcccgagca cctgcaaagc tgctggaact   420
tgcccgccgg atgtggttaa caaggttgaa ggtggcggtc ctaaaacctg caagcaagcg   480
ggcacctgcc cgagcgacgt gatcaacaaa gttgaaggcg tggcccgca ggcggagccg   540
gatcgtgcgc actacaacat tgtgaccttc tgctgcaaat gcgatggtgg cccgcaagcg   600
```

```
gaaccggatc gtgcgcacta taacattgtt acctttttgct gcaagtgcga tggtggcccg    660
caggcggaac cggaccgcgc gcactacaac atcgtgacct tttgttgtaa atgtgat        717
```

<210> SEQ ID NO 33
<211> LENGTH: 1017
<212> TYPE: DNA
<213> ORGANISM: Artificial
<220> FEATURE:
<223> OTHER INFORMATION: Trx/L2-8mer/FlankE7-3mer encoding

<400> SEQUENCE: 33

```
gagtacgatg cgagattga ctttaccaag ggccgtgttg ttctgtggtt tagcattccg    60
ggctgcggtc cgaagacctg caagcaagcg ggtacctgcc cgccggacat cattccgaaa   120
gtggaaggtg gcggtccgaa aacctgcaag caaagcggta cctgcccgcc ggatgttgtt   180
ccgaaagtgg agggcggtgg cccgcaaacc tgcaaggcgg cgggtacctg cccgagcgac   240
gttatcccga agattgaaca tggtggcccg cagacctgca aggcgaccgg cacctgcccg   300
ccggacgtga tcccgaaggt tgagggtggc ggtccgcgta cctgcaaagc ggcgggcacc   360
tgcccgccgg atgtgattcc gaaggttgaa ggcggtggcc ctcaaacctg caaactgact   420
ggcacttgcc cgccggacgt tattccgaag gttgagcatg tggcccgag cacctgcaaa    480 gctgctggaa cttgcccgcc ggatgtggtt aacaaggttg aaggtggcgg tcctaaaacc   540
tgcaagcaag cgggcacctg cccgagcgac gtgatcaaca agttgaagg cggtggcccg    600 caggcggagc cggatcgtgc gcactacaac attgtgacct tctgctgcaa atgcgatggt   660
ggcccgcaag cggaaccgga tcgtgcgcac tataacattg ttacctttg ctgcaagtgc    720 gatggtggcc cgcaggcgga accggaccgc gcgcactaca acatcgtgac cttttgttgt   780
aaatgtgatg gtggcccttg ccgtctggtt gagcgtttca tgaccgagct gagcgaatat   840
tttgaggata tccagattgt gcacatcaac gcgggcaagt ggaaaaacat cgttgacaag   900
tttaacattc tgaacgtgcc gacccgtgtt tacctgaaag atggtcgtga ggtgggtcgt    960 caaaaacctga tccgtagcaa agaggagatt ctgaagaaac tgaaagaact gcaggaa    1017
```

<210> SEQ ID NO 34
<211> LENGTH: 1188
<212> TYPE: DNA
<213> ORGANISM: Artificial
<220> FEATURE:
<223> OTHER INFORMATION: Trx/L2-8mer/FlankE7-3mer/IMX313 encoding

<400> SEQUENCE: 34

```
gagtacgatg cgagattga ctttaccaag ggccgtgttg ttctgtggtt tagcattccg    60
ggctgcggtc cgaagacctg caagcaagcg ggtacctgcc cgccggacat cattccgaaa   120
gtggaaggtg gcggtccgaa aacctgcaag caaagcggta cctgcccgcc ggatgttgtt   180
ccgaaagtgg agggcggtgg cccgcaaacc tgcaaggcgg cgggtacctg cccgagcgac   240
gttatcccga agattgaaca tggtggcccg cagacctgca aggcgaccgg cacctgcccg   300
ccggacgtga tcccgaaggt tgagggtggc ggtccgcgta cctgcaaagc ggcgggcacc   360
tgcccgccgg atgtgattcc gaaggttgaa ggcggtggcc ctcaaacctg caaactgact   420
ggcacttgcc cgccggacgt tattccgaag gttgagcatg tggcccgag cacctgcaaa    480 gctgctggaa cttgcccgcc ggatgtggtt aacaaggttg aaggtggcgg tcctaaaacc   540
tgcaagcaag cgggcacctg cccgagcgac gtgatcaaca agttgaagg cggtggcccg    600
```

-continued

```
caggcggagc cggatcgtgc gcactacaac attgtgacct tctgctgcaa atgcgatggt      660
ggcccgcaag cggaaccgga tcgtgcgcac tataacattg ttaccttttg ctgcaagtgc      720
gatggtggcc cgcaggcgga accggaccgc gcgcactaca acatcgtgac cttttgttgt      780
aaatgtgatg gtggcccttg ccgtctggtt gagcgtttca tgaccgagct gagcgaatat      840
tttgaggata tccagattgt gcacatcaac gcgggcaagt ggaaaaacat cgttgacaag      900
tttaacattc tgaacgtgcc gaccctggtt tacctgaaag atggtcgtga ggtgggtcgt      960
caaaacctga tccgtagcaa agaggagatt ctgaagaaac tgaaagaact gcaggaaggt     1020
agcaagaagc aaggcgacgc ggatgtgtgc ggtgaagttg cgtatatcca gagcgtggtt     1080
agcgattgcc acgttccgac cgcggaactg cgtaccctgc tggagattcg caagctgttt     1140
ctggagattc aaaaactgaa ggttgagggt cgtcgtcgtc gtcgtagc                  1188
```